(12) United States Patent
Goudy et al.

(10) Patent No.: US 12,263,277 B2
(45) Date of Patent: Apr. 1, 2025

(54) UNIAXIALLY-ALIGNED NANOFIBER SCAFFOLDS AND METHODS FOR PRODUCING AND USING SAME

(71) Applicant: Oridivus LLC, Decatur, GA (US)

(72) Inventors: Steven L. Goudy, Decatur, GA (US); Edward A. Botchwey, Decatur, GA (US)

(73) Assignee: Oridivus LLC, Decatur, GA (US)

( * ) Notice: Subject to any disclaimer, the term of this patent is extended or adjusted under 35 U.S.C. 154(b) by 0 days.

(21) Appl. No.: 16/780,596

(22) Filed: Feb. 3, 2020

(65) Prior Publication Data
US 2021/0001010 A1    Jan. 7, 2021

Related U.S. Application Data

(60) Provisional application No. 62/800,327, filed on Feb. 1, 2019.

(51) Int. Cl.
*A61L 27/54*  (2006.01)
*A61K 31/137*  (2006.01)
(Continued)

(52) U.S. Cl.
CPC .......... *A61L 27/54* (2013.01); *A61K 31/137* (2013.01); *A61L 27/16* (2013.01); *A61L 27/3691* (2013.01);
(Continued)

(58) Field of Classification Search
None
See application file for complete search history.

(56) References Cited

U.S. PATENT DOCUMENTS 6,191,334 B1    2/2001   Patterson
2011/0229551 A1*  9/2011   Doshi ............... D01D 5/0007
                                                514/180
(Continued)

FOREIGN PATENT DOCUMENTS

WO    WO-2012129073 A2 *  9/2012  ........... A61K 31/135
WO    WO-2018178313 A1 * 10/2018  ......... A61F 2/30907

OTHER PUBLICATIONS

Chou et al. ("Relationships between mechanical properties and drug release from electrospun fibers of PCL and PLGA blends" Journal of the Mechanical Behavior of Biomedical Materials, vol. 65, available online Sep. 9, 2016, pp. 724-733. (Year: 2016).*

*Primary Examiner* — Carlos A Azpuru
*Assistant Examiner* — Casey S Hagopian
(74) *Attorney, Agent, or Firm* — BEKIARES ELIEZER LLP

(57) ABSTRACT

Oral cavity wound healing occurs in an environment that sustains ongoing physical trauma and is rich in bacteria. Patients undergoing cleft palate repair have a high degree of wound healing complications, such as oronasal fistula (ONF) formation. Following hard palate injury, ONF was created that demonstrated little change in pro-regenerative monocytes LY6C$^{lo}$ monocytes; however, there were increased M2 macrophages observed. Delivery of FTY720 nanofiber scaffolds following hard palate injury prevented ONF formation, allowed complete wound healing and was associated with increased LY6C$^{lo}$ monocytes and pro-regenerative M2 macrophages. Evaluation of interleukin gene expression revealed reduction in pro-inflammatory IL1 and IL6 and increased expression of pro-regenerative IL10 with FTY720 nanofiber delivery. The ability of FTY720 scaffolds to increase LY6C$^{lo}$ monocytes, increase M2 macrophages and alter the interleukin expression during hard palate (Continued)

mucosal healing demonstrates the ability of a FTY720-based autotherapy to improve oral cavity wound healing.

14 Claims, 6 Drawing Sheets

(51) Int. Cl.
    *A61L 27/16*      (2006.01)
    *A61L 27/36*      (2006.01)

(52) U.S. Cl.
    CPC ....... *A61L 2400/06* (2013.01); *A61L 2400/12* (2013.01)

(56) References Cited

U.S. PATENT DOCUMENTS

| | | | |
|---|---|---|---|
| 2012/0004199 A1* | 1/2012 | Mcneil | A61P 29/00 514/165 |
| 2012/0213837 A1 | 8/2012 | Botchwey, III | |
| 2013/0171116 A1* | 7/2013 | Shoham | G01N 33/5058 424/93.21 |
| 2015/0100121 A1* | 4/2015 | Lu | B29C 67/04 623/13.12 |
| 2017/0290951 A1* | 10/2017 | Tavakol | A61L 27/22 |

\* cited by examiner

UNIAXIALLY-ALIGNED NANOFIBER SCAFFOLDS AND METHODS FOR PRODUCING AND USING SAME

CROSS REFERENCE TO RELATED APPLICATIONS

This application claims the benefit of and priority under U.S. Patent Application No. 62/800,327 filed Feb. 1, 2019, entitled "FTY-720 USED TO IMPROVE ORAL CAVITY WOUND HEALING," which is incorporated herein by reference in its entirety.

TECHNICAL FIELD

The present medical devices, including scaffolds and methods of using the same, relate generally to augmenting oral cavity wound healing and improving oronasal fistula prevention and recovery.

BACKGROUND

Oral cavity wound healing occurs in a bacteria laden environment that undergoes constant trauma and is exposed to saliva. Despite the frequency of injury to the oral cavity and its clinical significance, relatively little is known about the healing of oral mucosa and underlying bone. One particularly challenging problem is healing in the oral cavity following cleft palate repair, wherein all of the palate tissues are rotated to the midline to separate the nasal and oral cavities. Poor wound healing following cleft palate repair can occur in up to 60% of patients, leading to a persistent oronasal fistula (ONF), reflux of liquids from the nose, and air escape during speech. The presence of an ONF causes can velopharyngeal insufficiency, including inability to communicate and nasal reflux of liquids and solids. The morbidity of oral-nasal fistula is significant as the children have additional anesthesia, requiring overnight stay in the hospital and revision surgeries having an efficacy of 50%. The only available regenerative strategies to reduce ONF formation are from donated human material that are implanted as a barrier, carrying the risk of transmissible disease, rejection, and other complications.

Efforts to better understand host inflammation following injury have drawn interest for the development of novel autotherapies which are based on the body's natural ability to heal and protect itself. The role of pro-regenerative inflammatory signals in oral cavity wound healing is less well characterized compared to cutaneous wound healing but is known to have less scar and happen more quickly. Importantly, mononuclear cell infiltration, including monocytes and macrophages, is inherent to the post-injury microenvironment. Two distinct populations of monocytes exist in both mouse and human blood. Specifically, Ly6ChiCX3CR1lo "classical" monocytes in mice have been identified as a class of pro-inflammatory monocytes, whereas $Ly6C^{lo}CX3CR1hi$ non-classical, "anti-inflammatory" monocytes patrol the resting endothelium and exhibit pro-regenerative functions after injury. Monocyte-derived macrophages also respond to cues within the injury microenvironment that determine their role in wound healing responses and polarization state ranging from pro-inflammatory M1 macrophages to alternatively activated pro-regenerative M2a/c macrophages. In order to best implement this powerful repair system, an understanding of the properties of each cell type, their function within specific injury contexts, and their interaction with implanted biomaterials is necessary. Therefore, there is a long-felt but unresolved need for devices and methods that improve wound healing for ONF directly at the wound site by influencing the migration of wound healing cells thereto.

BRIEF SUMMARY OF THE DISCLOSURE

Briefly described, and according to one embodiment, aspects of the present disclosure generally relate to medical devices, including scaffolds and methods for using the same, for improved wound healing. The present disclosure describes novel approaches for recruitment of pro-regenerative non-classical monocytes using degradable nanofiber scaffolds loaded with immune modulatory drug FTY720 to improve oral cavity, mucosal, and other soft tissue wound healing.

Cleft palate formation occurs in up to 1 in 700 live births, and repair of the cleft palate is typically performed at a year of age. Once the cleft palate is repaired, patients may suffer the incidence of an oronasal fistula (ONF) due to wound healing problems, being this a hole in the repair site that allows for communication between the oral and nasal cavities. Incidence of ONF can go up to 63% after repair surgery, and children can have their feeding and speech affected. Persistence of an oral-nasal fistula (ONF) requires revision surgery, and the likelihood of ongoing ONF is 50% despite revision surgery.

Engineering exogenous control of the repair functions of mononuclear phagocytes may be the key to developing regenerative therapies in adult tissues and establishing the foundation for the new area of "immunoregenerative" biomaterial strategies. These materials seek to harness specific subpopulations of monocytes/macrophages to promote repair by influencing their recruitment, positioning, differentiation, and function within an injured tissue. In various embodiments, the present disclosure describes a murine (e.g., mouse) ONF model and autotherapies used to identify a mechanism by which oral cavity, soft tissue, and other mucosal healing can be augmented. According to one embodiment, after development of an ONF, wound healing can be improved by implanting an FTY720-releasing, uniaxially-aligned nanofiber scaffold directly to the wound site to control the monocyte population that migrates to the wound.

To understand the wound healing characteristics of the oral mucosa, the present disclosure provides an ONF model utilizing thermal injury for creating the ONF. In at least one embodiment, the ONF model permits study of the cellular and inflammatory infiltration to the wound site during the healing process. An exemplary analysis of FTY720 effects on ONF healing in the model includes, but is not limited to: 1) forming an ONF in each of a plurality of samples (e.g., mice); 2) dividing the mice into 3 groups, a no implant group, a group where blank nanofiber scaffolds are implanted, and a group where uniaxially-aligned nanofiber scaffolds with FTY720 are implanted; and 3) evaluating ONF healing results at predetermined time points (e.g., day 3, day 5, day 7, etc.).

FTY720 is a sphingosine-1-phosphate receptor analogue that is linked to $LY6C^{lo}$ (anti-inflammatory) monocytes and M2 (Pro-regenerative) macrophages attraction. According to one embodiment, for analysis of lymphocyte populations, cells are stained for flow cytometry with one or more of the following antibodies: Zombie NIR™ Fixable Viability Kit (Biolegend), PE anti-mouse MERTK (Mer) Antibody (Biolegend), Brilliant Violet 711™ anti-mouse CD64 (FcγRI) Antibody (Biolegend), Brilliant Violet 510™ anti-mouse Ly-6C Antibody (Biolegend), FITC anti-mouse CD206 (MMR) Antibody (Biolegend), Brilliant Violet 421™ anti-mouse/human CD11b Antibody (Biolegend). In various embodiments, to detect and sort for anti-inflammatory $LY6C^{lo}$ monocytes and M2 Macrophages, real-time polymerase chain reaction (PCR) analysis is performed with iQ SYBR green supermix (Bio-Rad, 1708882) in a Bio-Rad iCycler for 40 cycles to assess the expression of inflammatory IL-1, IL-4 and IL-6 and anti-inflammatory IL-10 and transcription factor Sox2, which is related to keratinocyte migration and proliferation. In one or more embodiments, slides are stained for H&E and Phospho-histone 3 to assess keratinocytes undergoing mitosis.

In at least one embodiment, data is analyzed using Graphpad prism 7 software, by analysis of variance (ANOVA) with Tukey's post-test. According to one embodiment, after 7 days, the no implant group shows slow healing of the ONF, but was unable to heal completely, which relates to human ONF after cleft palate surgery. In at least one embodiment, due to the inability of mice to ingest food and liquids, a mortality rate of more than 25% is experienced in mice used for ONF modeling. According to one embodiment, $LY6C^{lo}$ monocyte levels demonstrate a lack of change for the no implant group by 7 days, but M2 Macrophages showed a peak at the same endpoint. In various embodiments, in groups with implanted nanofiber scaffolds, the blank scaffold group shows no healing, while the FTY720 group shows healing, including reepithelization.

In one or more embodiments, by day 3 (e.g., post-ONF formation), flow cytometry analysis for the FTY720 group shows an increase in $LY6C^{lo}$ Monocytes and M2 Macrophages when compared to the blank group ($LY6C^{lo}$% of total cells=5.7%±0.6 for FTY720 vs. 3.7%±0.9 for Blank) ($LY6C^{lo}$% of total CD11B+ cells =22.5±5.6 for FTY720 vs. 12.7±5.7 for blank) (M2 Macrophages % of total cells=3.7±0.5% for FTY720 vs. 1.4±0.2% for blank) (M2 Macrophages % of Macrophages=63.6±3.9 for FTY vs. 34.7±6.4% for blank).

In various embodiments, by day 5 increased Phosphohistone-3 activity is observed, which is a visual representation of cells undergoing mitosis (for example, keratinocyte proliferation of 8.1 vs. 4.1 cells per high power field). In one or more embodiments, the FTY720 scaffold group demonstrates a decrease in IL-1, IL-4 and IL-6 (e.g., pro-inflammatory interleukins) and an increase in IL-10 (e.g., pro-regenerative interleukin).

In at least one embodiment, ONF creation in murine models following thermal injury is a useful tool to study ONF formation. According to one embodiment, a high base line population of anti-inflammatory monocytes can be identified and, following injury (e.g., ONF formation), an increased level of M2 macrophages can be identified, thereby suggesting that the oral cavity has supportive wound healing characteristics present. In various embodiments, as described herein, animals that receive local delivery of FTY720 through nanofiber scaffolds demonstrate greater injury healing and ONF prevention. Due to expression of Sphingosine-l-phosphate receptor 3 in anti-inflammatory monocytes and M2 macrophages, the greater injury healing and ONF prevention can reduce or prevent functionality impairments, such as the inability to ingest foods and liquids. According to one embodiment, controlling the oral cavity's abilities to increase anti-inflammatory monocytes and M2 macrophages provides a regenerative therapy to improve oral cavity wound healing.

According to a first aspect, an implantable scaffold including: A) a plurality of nanofibers forming a substantially flat portion; B) wherein the plurality of nanofibers are uniaxially aligned; and C) wherein each of the plurality of nanofibers includes polycaprolactone (PCL), poly(lactic-co-glycolic-acid) (PLGA), and S1P1 agonist.

According to a second aspect, the implantable scaffold of the first aspect or any other aspect, wherein the S1P1 agonist is FTY720.

According to a third aspect, the implantable scaffold of the second aspect or any other aspect, wherein each of the plurality of nanofibers includes PCL and PLGA at a predetermined weight ratio between about 20:80 and 80:20 wt./wt.

According to a fourth aspect, the implantable scaffold of the third aspect or any other aspect, wherein: A) the predetermined weight ratio of PCL and PLGA is about 1:1 wt./wt.; and B) each of the plurality of nanofibers includes FTY720 at about a 1:200 drug:polymer weight ratio.

According to a fifth aspect, the implantable scaffold of the fourth aspect or any other aspect, wherein the substantially flat portion includes a disk-like shape.

According to a sixth aspect, the implantable scaffold of the fourth aspect or any other aspect, wherein the plurality of nanofibers includes inter-fiber distances of about 50 µm.

According to a seventh aspect, a method for treating an oral wound cavity, including implanting a scaffold at an oral cavity wound site of a patient, wherein: A) the scaffold includes a plurality of nanofibers forming a substantially flat portion; and B) each of the plurality of nanofibers includes polycaprolactone (PCL), poly(lactic-co-glycolic-acid) PLGA, and S1P1 agonist.

According to an eighth aspect, the method of the seventh aspect or any other aspect, wherein the plurality of nanofibers are uniaxially aligned.

According to a ninth aspect, the method of the eight aspect or any other aspect, wherein: A) the S1P1 agonist is FTY720; and B) each of the plurality of nanofibers includes PCL and PLGA at about a 1:1 wt./wt. ratio.

According to a tenth aspect, the method of the ninth aspect or any other aspect, wherein each of the plurality of nanofibers includes FTY720 at about a 1:200 drug:polymer weight ratio.

According to an eleventh aspect, the method of the ninth aspect or any other aspect, wherein each of the plurality of nanofibers includes FTY720 at about a 1:20 drug:polymer weight ratio.

According to a twelfth aspect, the method of the ninth aspect or any other aspect, wherein each of the plurality of nanofibers includes FTY720 at about a 1:2000 drug:polymer weight ratio.

According to a thirteenth aspect, a method for fabricating a wound-healing scaffold, including: A) dissolving, at a predetermined weight ratio, polycaprolactone (PCL) and poly(lactic-co-glycolic-acid) (PLGA) in a solution of methanol and chloroform to create a mixture; B) adding to the mixture an S1P1 at a second predetermined weight ratio; C) agitating the mixture for a predetermined time period; D) electrospinning the mixture at a predetermined flow rate, a predetermined applied voltage, and a predetermined working distance to produce a plurality of nanofibers, wherein the plurality of nanofibers are arranged into one or more nanofiber sheets; and E) extracting, from the one or more nanofiber sheets, a plurality of nanofiber scaffolds, wherein each of the plurality of nanofiber scaffolds includes a substantially flat portion.

According to a fourteenth aspect, the method of the thirteenth aspect or any other aspect, wherein: A) the plurality of nanofibers are uniaxially aligned; B) the S1P1 agonist is FTY720; C) the predetermined weight ratio is about 1:1 wt./wt.; D) the solution includes the methanol and chloroform at about a 1:3 volume ratio; and E) the second predetermined weight ratio is about a 1:200 drug:polymer weight ratio.

According to a fifteenth aspect, the method of the fourteenth aspect or any other aspect, wherein: A) the predetermined flow rate is about 1 mL/hr; and B) the predetermined applied voltage is about 19 kV.

According to a sixteenth aspect, the method of the fifteenth aspect, or any other aspect, wherein: A) the predetermined time period is at least 2 hours; and B) the predetermined working distance is about 12 cm.

According to a seventeenth aspect, the method of the fifteenth aspect or any other aspect, further including, prior to the electrospinning, loading about 2 mL of the mixture into a 3 mL syringe with a 10 mm diameter, wherein the mixture is electrospun from the 3 mL syringe.

According to an eighteenth aspect, the method of the seventeenth aspect or any other aspect, further including: A) wrapping the one or more nanofiber sheets in low-binding folders; and B) storing the one or more nanofiber sheets at about −20 degrees Celsius.

According to a nineteenth aspect, the method of the eighteenth aspect or any other aspect, wherein the mixture includes a polymer concentration of about 20%.

According to a twentieth aspect, the method of the nineteenth aspect or any other aspect.

These and other aspects, features, and benefits of the claimed invention(s) will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE FIGURES

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment, and wherein:

FIGS. 1G-H show exemplary nanofiber scaffold structures, according to one embodiment of the present disclosure.

FIG. 2A shows a patient following two prior attempts to close an oral nasal fistula after palate repair (arrows).

FIGS. 2B-D show diagrams illustrating implementations of the technology described herein, according to one embodiment of the present disclosure.

FIG. 3 illustrates an exemplary oral injury creation process, according to one embodiment of the present disclosure.

FIG. 4 shows a graph of mice mortality following an exemplary oral cavity ONF formation process, according to one embodiment of the present disclosure.

FIGS. 5A-D shows exemplary oral injury healing results, according to one embodiment of the present disclosure.

FIGS. 6A-G show graphs of exemplary monocyte and macrophage migration into injured hard palates, according to one embodiment of the present disclosure.

FIGS. 7A-C illustrate an exemplary FTY720 scaffold-assisted ONF healing process, according to one embodiment of the present disclosure.

FIGS. 11A-D show graphs of $LyC6^{lo}$ monocyte percentages in exemplary ONFs with blank or FTY720 scaffolds, according to one embodiment of the present disclosure.

FIGS. 12A-F show graphs of macrophage migration in exemplary ONFs with blank or FTY720 scaffolds, according to one embodiment of the present disclosure.

FIGS. 13A-C show graphs of hard palate mucosa interleukin expression following injury and implantation with exemplary blank or FTY720 nanofiber scaffolds, according to one embodiment of the present disclosure.

FIGS. 14A-I show graphs of exemplary monocyte and macrophage migration into injured hard palates with exemplary implanted blank or FTY720 nanofiber scaffolds, according to one embodiment of the present disclosure.

FIGS. 15A-D show graphs of monocyte percentages in ONFs with implanted exemplary blank or FTY720 nanofiber scaffolds, according to one embodiment of the present disclosure.

FIGS. 16A-F show graphs of exemplary monocyte and macrophage migration into injured hard palates with exemplary implanted blank or FTY720 nanofiber scaffolds, according to one embodiment of the present disclosure.

FIG. 17 illustrates μCT images of exemplary hard palate reconstruction results, according to one embodiment of the present disclosure.

FIG. 18 illustrates exemplary μCT imagery of the hard palate showing the vascularity of the normal palate, with the greater palatine artery (red) and associated smaller capillaries (green) that can be quantified.

FIG. 19 illustrates an exemplary nanofiber scaffold-augmented wound healing process described herein, according to one embodiment of the present disclosure.

DETAILED DESCRIPTION

Figure 1B:
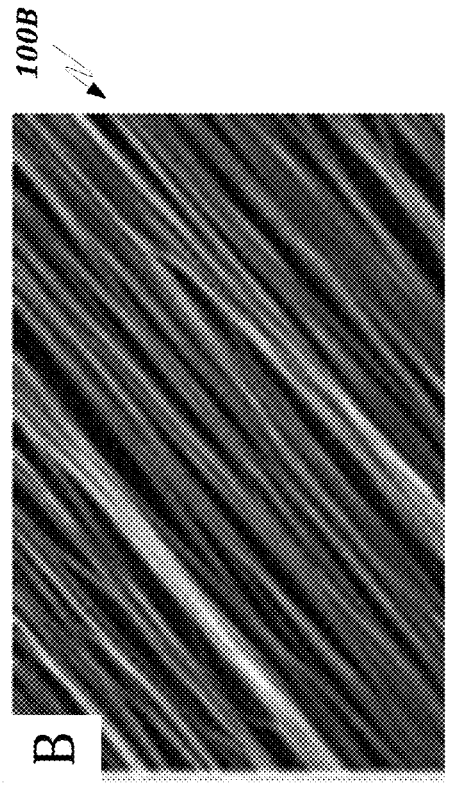
FIGS. 1A-F show scanning electron microscope (SEM) images of various nanofiber structures described herein, according to one embodiment of the present disclosure.

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Whether a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

Overview

Aspects of the present disclosure generally relate to uniaxially-aligned nanofiber scaffolds for treating oral cavity wounds, such as, for example, oronasal fistulae (ONF).

Significance

Cleft palate formation is the most common craniofacial anomaly in children and occurs in 1:1000 live births. All of these patients undergo multiple surgeries during their lifetime and, for many, the first surgery is the repair of their cleft palate. Unfortunately, up to 60% of cleft palate patients suffer poor wound healing following repair and develop an oral nasal fistula (ONF), with a continued communication between the oral and nasal cavities. ONF formation affects the daily life of the patient with continuing oro-nasal reflux of food and liquid out of the nose and speech problems due to air leakage from the nose. Persistence of the ONF, despite re-repair, occurs in 50% of patients, and the need for additional surgeries that require the use of local, regional or free tissue transfer is higher in this patient population. To try to reduce the frequency of persistent ONF, some surgeons use human dermal matrix; however, there is a risk for prion/viral transmission to the child and the dermal matrix is only functioning as a barrier, not as a regenerative therapy. The high frequency and recurrence of ONF, along with the risks related to repeated anesthesia needed for re-repair, highlight the need for a regenerative approach to improve oral cavity wound healing following cleft palate repair.

Regenerative approaches to wound healing have primarily focused on cutaneous wound healing conditions such as venous stasis ulcers and burn would healing. Cutaneous wound healing has been widely studied and includes a well-orchestrated series of stages: hemostasis, inflammation, epithelialization, and maturation. The inflammatory phase begins immediately following hemostasis and is associated with the creation of free radicals to kill any pathogens. The inflammatory phase can also include extravasation of leukocytes into the wound bed. The type and density of the inflammatory cells present determine factors including, but not limited to: 1) the amount of free radical production; 2) the time until resolution of the inflammatory phase; and 3) the timing of revascularization of the wound bed. An increased inflammatory phase during cutaneous wound healing can be associated with hypertrophic scar formation and delayed wound healing.

Oral cavity wound healing is less well characterized compared to cutaneous wound healing. For example, the oral cavity heals more quickly and demonstrates less scar tissue formation compared to cutaneous wound healing. Oral cavity wound healing occurs in a bacteria laden environment that undergoes constant trauma by the actions of the tongue during eating and is exposed to saliva. Wound healing following cleft palate repair involves all of the hard palate mucosa, where all of the palate tissues are rotated to the midline to separate the nasal and oral cavities. Poor wound healing following cleft palate repair has been reported to occur in up to 60% of patients; when this occurs a persistent oronasal fistula (ONF) develops leading to reflux of liquids from the nose and air escape during speech. Currently the only available strategies to reduce ONF formation by implanting donated human dermis as a barrier between the oral and nasal mucosa or delivering platelet rich plasma, carrying the risk of transmissible disease, rejection, and other complications.

A critical part of tissue repair occurs during the inflammatory stage, the inflammatory stage being contingent on the mobilization of circulating monocytes into the wound bed. Based on local factors, these monocytes undergo differentiation into inflammatory (IM) and anti-inflammatory (AM) monocytes. Murine monocytes can be categorized by many markers including Ly6C that can be used in flow sorting. The expression of cytokines between these two types of monocytes is very different, and in mice the inflammatory monocytes (based on the expression of $Ly6^{hi}$) secrete large amounts of TNFa and IL1 to stimulate phagocytosis, whereas the anti-inflammatory monocytes (based on the expression of $Ly6C^{lo}$) monocytes secrete large amounts of IL4 and IL10 to stimulate regeneration. Because previous studies have primarily been performed during cutaneous wound healing, there is little information about the migration of inflammatory and anti-inflammatory monocytes into oral cavity wounds.

Most recruited monocytes differentiate into a wide spectrum of macrophages that are responsible for the long-term promotion of repair. Macrophages are highly responsive to cues from their environment and can dynamically modify their phenotype and behavior. Though their phenotypes in vivo are highly varied, they are broadly classified into two phenotypes, classically-activated (M1) or alternatively-activated (M2), with the M2 class possessing multiple subtypes. M1 macrophages are primary players in pathogen destruction, they secrete inflammatory cytokines (TNF-a, IL-6), and drive h1-type responses; whereas M2 macrophages are associated with pro-regenerative activities including angiogenesis, promotion of extracellular matrix deposition, secretion of anti-inflammatory cytokines (TGF-β, IGF-1, IL-10), and resolution of inflammation.

Macrophages govern nearly all stages of tissue repair and are required for effective healing, which has been demonstrated by depletion studies in a wide array of injured tissues such as skeletal muscle, skin, myocardium, and cornea. What is not currently known is how the monocytes and macrophages interact with the oral cavity during wound healing and what cytokines are present during each phase of wound healing. Unique to the oral cavity is the constant physical trauma of the wounds due to swallowing and eating, and the presence of bacteria and saliva likely also contribute to the inflammatory response by the tissue.

Strategies for treating oral cavity wounds require the delivery of multiple cues for initiating and promoting endogenous repair programs. For example encouraging the recruitment of these monocytic progenitors to oral cavity wounds may elevate wound-healing macrophage levels in the tissue, shifting the inflammatory tone towards the promotion of repair. To achieve the selective recruitment of $Ly6C^{lo}$ (regenerative) monocytes to oral cavity wounds, the present disclosure contemplates utilizing the local delivery of FTY720, a novel recruitment cue acting through the Sphingosine 1-phosphate (S1P) signaling axis that redirects $Ly6C^{lo}$ monocytes from circulation to injured tissue. S1P is a bioactive lipid that exerts pleiotropic effects on cells via 5 cognate G-protein coupled receptors (S1P-5). S1P2 and S1P3 are both expressed on circulating monocytes. In at least one embodiment, $Ly6C^{hi}$ and $Ly6C^{lo}$ monocytes may be functionally distinguished by low and high expression of S1P3, respectively. According to one embodiment, the high S1P3 expression of non-classical monocytes can be leveraged as a functional target to draw the non-classical monocytes from circulation into injured tissues.

In one or more embodiments, the S1PR agonist FTY720 is differentially released from polymers for controlled release ("acid-capped" L-A and "methyl-ester capped" H-ME polymers). In various embodiments, in both polymer groups, FTY720 is released with an initial burst in the first hours of incubation in vitro, followed by a delay and a second phase of release between 3 and 5 days. According to one embodiment, an immunoregenerative approach is executed to control how M1 to M2 are spatially and temporally regulated by recruitment of anti-inflammatory monocytes (AM). In at least one embodiment, the immunoregenerative approach includes determining how localized administration of FTY720 is compartmentalized in vivo. In one or more embodiments, the phosphorylated form of the drug FTY720-P is primarily responsible for receptor mediated signaling and has much lower threshold effective concentrations than FTY720 at all of the S1PRs. In at least one embodiment, similar to S1P, FTY720-P must be dephosphorylated by LPP3 to enter the cell. According to one embodiment, once inside the cell, FTY720 can be phosphorylated by sphingosine kinase 2 (SPHK2) and subsequently exported from the cell by Spns2. In various embodiments, the ability of FTY720 to be reversibly phosphorylated allows it to undergo multiple cycles of signaling in the tissue, contributing to a sustained gradient. According to one embodiment, the regulatory roles of local gradients of FTY720 and FTY720-P are differentiable.

In one example, FTY720 and FTY720-P are released from 1 mm diameter thin films in a cutaneous dorsal skinfold window chamber for 3 days to investigate the in vivo gradient produced by H-ME PLGA film release of S1P receptor targeting compounds. In the same example, the FTY720 delivered during cutaneous wound healing recruits AM monocytes and is associated with increased vascularity and improved wound healing, thereby demonstrating potential efficacy in improving wound healing in the oral cavity.

Oral Nasal Fistula Model That Recapitulates the Human Condition

The occurrence of ONF following cleft palate repair occurs in up to 60% of cleft palate patients and is a significant burden to their health and is associated with increased healthcare costs. To date, there has not been a reliable model to study the occurrence of ONF and therefore there are not any current regenerative therapies being developed. In various embodiments, the present disclosure provides an ONF model that recapitulates the human phenotype that has functional outcome measures, thereby allowing investigation of wound healing, and the testing of regenerative therapies.

Characterizing the Immune Profile During Palate Wound Healing and ONF Formation

The composition of the monocyte population during oral cavity wound healing is unknown. In one or more embodiments, the present disclosure identifies the critical cell populations and the associated inflammatory mediators of cell recruitment and cell differentiation during palate wound healing.

Determining the Inflammatory Cytokine Profile During ONF Formation

Oral cavity wound healing is not as well understood as cutaneous wound healing, and the primary model for studying injuries to the oral cavity is periodontal disease. Palate wound healing is clinically distinct from periodontal disease due to the absence of teeth, plaque and biofilm and there a different cytokine expression signature. According to one embodiment, the present disclosure identifies the predominant cytokine profile during oral cavity wound healing, potentially supporting the development of immunomodulation of the wound healing response.

Harnessing Autotherapy Delivery to Improve Palate Wound Healing

There are currently no regenerative strategies which focus on harnessing the immune system to improve palate wound healing. In one or more embodiments, the present disclosure provides successful, efficacious strategies to selectively harness the anti-inflammatory monocyte and macrophage population to improve cutaneous wound healing. In at least one embodiment, the present disclosure provides a biomaterial nanofiber construct to control the spatiotemporal delivery of FTY720 to induce the migration of pro-regenerative monocytes to ONF.

Determining the Contributions of the Inflammatory Response During ONF Formation, Identifying Key Regulatory Cytokine and Gene Pathways Expressed According to one embodiment, during palate wound healing, the pro-inflammatory monocyte migration pathway is the predominant and conserved response to injury, and is associated with increased pro-inflammatory cytokines and has a high rate of ONF formation. In one or more embodiments, the present disclosure provides determinations of the composition and contribution of monocyte recruitment during palate wound healing and ONF formation and determine functional outcomes associated with ONF formation. In at least one embodiment, the present disclosure identifies the associated inflammatory response in the tissue and in the serum during palate wound healing. In various embodiments, the present disclosure describes, following ONF creation, detecting the associated expression of cytokines, particularly interleukins (IL1 and IL6) using multiplex analysis and alterations in the gene transcription pathways using RNA-seq focused on inflammation, epithelial repair, and extracellular matrix production.

Scientific Premise and Feasibility

Oral cavity mucosal wound healing has previously been studied by creating superficial palate mucosal wounds that completely re-epithelialize over a 7 day period, however this model does not replicate ONF formation. Using palate mucosal injury models, investigators have also evaluated the delivery of multiple different therapeutics to aid in the superficial wound healing including VEGFa and Thymosin B4. These studies analyzed the inflammatory, histologic, and transcriptional differences between cutaneous and oral cavity wound healing and suggested that therapeutic approach can successfully improve oral cavity wound healing, however they did not use an ONF model. In a separate study, a mini-pig model of ONF was created; however, these animals did not suffer from feeding difficulties and the relative size of the ONF created was small (e.g., and therefore not representative of the normal clinical condition seen in children with ONF). Without intervention, the mini-pigs had persistence of their small asymptomatic ONF, and this study evaluated multiple different types of implantable human-derived therapies to act as a barrier during the healing of the ONF. These therapies were not designed to provide regenerative cues to the local tissue during wound healing and the outcomes were variable with a limited sample size.

In various embodiments, chronic wounds, whether cutaneous or oral, demonstrate chronic persistence of pro-inflammatory subsets of mononuclear phagocytes (MPs) and insufficient input from anti-inflammatory subsets that promote resolution of inflammation could lead to compromised wound healing. Thus, to engineer an immunomodulatory therapeutic approach that leads to regenerative oral cavity wound healing, a thorough understanding of the phases of wound healing is needed, specifically the inflammatory component. Furthermore, the relationship between the timing of monocyte infiltration and associated cytokine production and associated gene transcription during oral cavity wound healing are poorly understood and have not been investigated in the context of ONF formation. Therefore, the design of therapeutic interventions that target pro-regenerative monocytes requires an understanding of the local cues that determine the monocyte and macrophage migration and how these cues can be therapeutically targeted.

Development of a Murine ONF With Measurable Functional Outcomes

According to one embodiment, injury to the hard palate oral and nasal mucosa in mice recapitulates the ONF phenotype seen in children. ONF formation in children, due to wound healing complications following cleft palate repair, can cause speech issues and reflux of food and water from their nose, affecting their ability to gain weight.

To produce a Murine ONF model, 12 week old C57/b6 mice are obtained (for example from Jackson Laboratories) and anesthetized using intraperitoneal ketamine. According to one embodiment, the oral cavity is accessed using a retractor while the mice are spontaneously breathing. In one or more embodiments, a punch biopsy is used to create a 1.5 mm hard palate mucosal full thickness injury through oral and nasal mucosa in the midline, to avoid the palatine arteries laterally. In various embodiments, mice are divided into the 2 groups: no treatment (control) and hard palate injury alone. Each group includes 10 mice per group per time point, (10 male and 10 female mice). The time points include 0, 3, 5, and 7 days and healing of the ONF is assessed using histomorphometry while functional outcomes are measured evaluating for poor oral intake measured by body weight loss, dehydration (serum sodium using an ELIZA assay), and eventual death (Kaplan Meir curve).

Determining the Critical Healing Time Point(s) During Palate Wound Healing Using an ONF Model According to one embodiment, similar to humans, the critical wound healing time point is immediately following hard palate injury (or surgery) and fistula healing is unlikely after this critical time period. To assess the critical wound healing time, in at least one embodiment, ONFs are created in Murine models and standard histomorphologic evaluation of the mice following injury at day 0, 3, 5, 7, and 14 days is performed. According to one embodiment, the specimens are assessed using H+E staining of coronal sections in 10 mice (10 male and 10 female) each to evaluate: the width of the ONF, the presence or absence of inflammatory infiltrate at the wound edges, the formation of a basement membrane in the healing areas (using type IV collagen and laminin staining). In at least one embodiment, the exposure of the maxillary and palatine bones as well as the surrounding maxillary structures are evaluated using micro-computed tomography (μCT) imaging.

According to one embodiment, ONF area width is measured at each of the time points and compared to controls. In at least one embodiment, ONF Morphology: Confirmation of ONF formation is performed using H+E, PECAM, laminin and type 4 collagen staining on frozen sections of mice at the above time points done in 10 mice to evaluate the timing and strength of signal with comparison to control using ImageJ. In various embodiments, μCT imaging is performed to evaluate the maxillary bone formation. For example, μCT measurements are used detect any underlying bony destruction due to ONF formation. In at least one embodiment, sequential trans-axial images through the palatal bones are obtained using μCT40 imaging. In one or more embodiments, contours are drawn around the defect and regenerated tissue region, the maxillary bone, the palatine bone as well as other maxillary structures. According to one embodiment, evaluations are run for bone mineral density (BMD), bone volume (BV) and bone volume fraction (BV/TV) using a standard Scanco script. In various embodiments, to measure the proliferative and apoptosis response following oral injury, proliferation and apoptosis are assessed. In at least one embodiment, to assess proliferation and apoptosis, serial coronal sections through the anterior, middle and posterior regions of the oral injury are performed sequentially at the above time points and the sections are stained with phosphohistone-H3 (PH3) and TUNEL, to detect proliferation and apoptosis, respectively. In one or more embodiments, the total proliferative/apoptotic index is the PH3/TUNEL-+ cells divided by the total cells per high power field in 10 samples, from male and female mice.

Measuring the Timing and Contribution of the Inflammatory Infiltrate During ONF Healing According to one embodiment, during oral cavity wound healing following injury, there is predominantly a pro-inflammatory lymphocytic infiltrate. In various embodiments, analysis of the cell composition in the hard palate mucosa is performed for 10 male and 10 female mice (e.g., the hard palate mucosa is removed, following hard palate injury, from the alveolar ridge extending to the soft palate). In one or more embodiments, interleukin (IL) assessment (e.g., assessment of inflammatory mediators (IL 1, 6 and 10) during ONF wound healing) is performed. According to one embodiment, the IL assessment is performed in samples with and without scaffold placement, and includes using quantitative PCR of hard palate mucosa at day 3, 5, and 7 and comparing results to controls. In at least one embodiment, serum is collected and evaluated for levels of IL1, IL6, IL10 and VEGF using ELIZA to determine if there are systemic alterations in inflammatory and vasculogenic gene regulation and compared to uninjured controls.

In various embodiments, flow cytometry of inflammatory cells is performed to characterize monocyte and macrophage phenotypes. In one or more embodiments, for analysis of lymphocyte populations, hard palate mucosa is harvested and digested in 1 mg/ml collagenase I (Sigma) for 45 minutes at 37 degrees Celsius. In at least one embodiment, the digested mucosa is filtered through a cell strainer to obtain a single cell suspension. According to one embodiment, the single-cell suspensions are stained for live cells using either Zombie Green or Zombie NIR (Biolegend) dyes in cell-culture grade PBS per manufacturer instructions. In various embodiments, cells are stained with cell phenotyping antibodies in a 1:1 volume ratio of 3% FBS and Brilliant Stain Buffer (BD Biosciences) according to standard procedures and analyzed on a FACS AriaIIIu flow cytometer (BD Biosciences). In one or more embodiments, antibodies used for monocyte and macrophage cell phenotyping include one or more of, but are not limited to: BV605-conjugated CD4 (Biolegend), BV785-conjugated CD8 (Biolegend), PE-Cy7-conjugated CD3ε (Biolegend), PE-conjugated anti-CD115 (BioLegend), PerCP-Cy5.5-conjugated anti-CD115 (BioLegend), PE-conjugated anti-CD25, FITC-conjugated anti-FoxP3 (eBioscience), BV510-conjugated anti-CD11b (BioLegend), BV421-conjugated anti-CD11b (BioLegend), BV510-conjugated APC (BioLegend), APC conjugated anti-Ly6C (BioLegend), BV711-conjugated anti-CD64 (BioLegend), PE-conjugated anti-MerTK (Biolegend), APC-Cy7-conjugated anti-Ly6G (BioLegend), PE-Cy7 conjugated anti-CD206 (BioLegend), FITC-conjugated anti-CD206 (BioLegend), APC-conjugated Lineage antibody cocktail (BD Pharmigen), PE-Cy5 conjugated anti-CD29 (BioLegend), and PerCP-Cy5.5-conjugated anti-CXCR4 (BioLegend). According to one embodiment, 30 µL of Accucheck Counting Beads (Invitrogen) are added per sample for absolute quantification of cell populations.

Measuring the Changes in Inflammatory Cytokines and Gene Expression During ONF Formation According to one embodiment, formation of a connection between the oral and nasal cavity is associated with an initial burst of high levels of pro-inflammatory cytokines and genes, which is followed by the production of pro-regenerative cytokines and genes later at day 5 and 7 as the ONF heals. In at least one embodiment, hard palate mucosa of mice for cytokine and RNA-seq are collected prior to oral injury (Aim 1a) and at day 3, 5, and 7 following injury from 5 male and 5 female mice. In various embodiments, a cytokine analysis (such as, for example, a Chemokine 36 array, Thermo Fisher) is performed (for example, in the Emory Multiplex Assay Core). In one or more embodiments, RNA-seq data are generated (for example, using the Emory Genomics Core). In at least one embodiment, about 50 million paired-end 100 nt reads per sample are mapped to the human reference genome using the R/Bioconductor package DEXSeq, which is optimized for robust inference of annotated exon usage, and uses a generalized linear model for hypothesis testing accounting for biological and technical variability. According to one embodiment, quantitative polymerase chain reaction (PCR) is performed on the cells to confirm changes noted by RNA-seq. In various embodiments, Pathway analysis of RNA-seq data using Ingenuity software package (Qiagen) is performed and focuses on proliferation, differentiation, migration, angiogenesis and extracellular matrix production.

Statistical Analysis

According to one embodiment, each experiment is independently repeated three times on independent biologic samples and differences between groups (control and ONF) and sex are tested by two-way analysis of variance with 2 degrees of freedom for the treatment main effect, 3 degrees of freedom for time, and 6 degrees of freedom for treatment x time interaction. In at least one embodiment, based on preliminary experiments, it is estimated that 80% power for the main effects of Treatment to detect effect sizes explains 50% or more of the variance of each transcript at a False Discovery rate of 10% (typically p<0.001, ~100 transcripts).

Outcomes

According to one embodiment, the oral cavity mucosal healing occurs over a 7 day period. In various embodiments, during that time, there is active wound reparative response, with significant monocyte and macrophage infiltration to the area. In one or more embodiments, there is a strong contribution of pro-inflammatory monocytes that are recruited to the area, due to the ongoing physical trauma (from eating) and high density of bacterial exposure. Similarly, in at least one embodiment, there is an increased concentration of Ly6C$^{hi}$ inflammatory monocyte (IM) percentage, similar to what is reported during bowel mucosal injury and inflammation measured by flow cytometry. According to one embodiment, amplified expression of inflammatory cytokines (IL 1 and 6) is increased, similar to that seen during bowel mucosal healing. Additionally, in one or more embodiments, proliferation and apoptosis are high (e.g., due to the presence of inflammation). In various embodiments, PECAM imaging (vascularization) demonstrates the presence of immature vascular channels within the granulation tissue at the wound edges.

According to one embodiment, healing of an ONF in Murine models does not occur after 7 days (e.g., unlike the previous mouse models that only created a partial mucosal injury) due to ongoing passage of fluid and food through the fistulous tract. In at least one embodiment, the inability of mice with ONF to eat and drink is associated with increased mortality (e.g., that is studied using a Kaplan Meir curve) and increased serum sodium levels, indicating dehydration. In one or more embodiments, evaluation of the exposed palatine bone in the ONF may not undergo necrosis or develop osteomyelitis, as this is not typically seen in human patients with ONF. In various embodiments, the initial inflammatory response following oral cavity injury is predominantly an increase in Ly6C$^{hi}$ inflammatory (IM) monocyte percentage of CD11B+ cells compared to Ly6C$^{lo}$ (e.g., determined to be SSCloCD45+CD11b+Ly6C−Gr1− using flow cytometry). According to one embodiment, at day 3, there are increased levels of pro-inflammatory cytokines IL1 and IL6, along with increased transcription of inflammatory pathway genes, including interleukins, with the later expression of reparative gene programs involving basement membrane production and epithelial differentiation at days 5 and 7.

Engineering a Nanofiber Scaffold to Provide Controlled Spatial and Temporal Delivery of FTY720 to Improve Palate Wound Healing Using an Autotherapeutic Approach According to one embodiment, during palate wound healing, a conserved monocyte recruitment pathway can be tuned to improve oral wound healing and reduce ONF formation. In various embodiments, the delivery of nanofiber-FTY720 scaffolds during oral wound healing are observed to determine the optimal FTY720 concentration, nanofiber configuration and resultant changes in the pro-regenerative monocyte recruitment and altered cytokine and gene expression. In at least one embodiment, FTY720 scaffold success is determined based on objective measurements of the wound healing time, angiogenesis, functional outcomes (dehydration and survival), cell subtype and response to FTY-720 during palate wound healing.

Scientific Premise and Feasibility

In various embodiments, monocytes are a key component of wound healing and are present during both cutaneous and oral cavity wound healing. According to one embodiment, oral cavity wounds have fewer monocytes present compared to cutaneous wounds. In one or more embodiments, circulating monocytes in mice take on a pro-inflammatory ($Ly6C^{hi}$) or a pro-reparative ($Ly6C^{lo}$) phenotype. In at least one embodiment, once in the tissue, the monocytes differentiate into macrophages that also play an important role in wound repair and can be broadly categorized between two phenotypes M1 (inflammatory) or M2 (pro-reparative) (e.g., though a wide spectrum of sub-types exist). In various embodiments, inhibition of M2 macrophage production is associated with prolonged wound healing and more inflammation, suggesting that M2 macrophages are critical to reduced scarring and inflammation. In one or more embodiments, the secretion of interleukins during oral wound healing is critical, as inhibition of their function is associated with reduced macrophage infiltration, angiogenesis, and collagen deposition. According to one embodiment, during wound healing, monocytes and macrophages produce multiple cytokines, particularly ILL during the immediate inflammatory response. In various embodiments, high levels of IL1 are associated with poor wound healing; however, complete loss of IL1 leads to delayed wound healing, particularly in the oral cavity.

In at least one embodiment, pro-regenerative interleukins (including IL10) are produced during wound healing and can be described as pro-regenerative cytokines. In one or more embodiments, improved wound healing is experienced with IL10 delivery.

Multiple approaches can be used to improve the recruitment of the pro-regenerative monocytes and macrophages to cutaneous wounds. In at least one embodiment, FTY720, a sphingosine analog, demonstrates efficacy in attracting pro-regenerative monocytes to a cutaneous wound. According to one embodiment, the delivery of FTY720 on a nanofiber scaffold increases the frequency of $Ly6C^{lo}$ pro-regenerative monocytes at 3 days and is associated with improved wound healing. In one or more embodiments, FTY720 increases the migration of M2 macrophages into a wound bed. In various embodiments, there are numerous small molecule analogs of S1P that can be used to selectively perturb specific S1P receptors, and one that demonstrates particular success is FTY720, an S1P1 and S1P3 agonist. For example, local delivery of FTY720 to inflamed microvasculature in the dorsal skinfold window chamber ("backpack") model selectively recruits non-classical $Ly6C^{lo}$ monocytes to inflamed tissues. In the same example, based on flow cytometry, FTY720 significantly increases the proportion of anti-inflammatory monocytes (AMs) relative to unloaded nanofiber scaffolds.

Design of therapeutic interventions that target mononuclear phagocytes (MPs) requires an understanding of the trafficking patterns and fate determination of distinct cell subsets. According to one embodiment, novel poly (lactic co-glycolic acid)/polycaprolactone nanofibers are utilized to control local the spatiotemporal delivery of FTY720 and subsequently S1P signaling in the microenvironment of the injured tissues.

In at least one embodiment, nanofiber scaffolds are suitable as delivery vehicles due to their tunable properties and ability to be spun in specific geometries. In one or more embodiments, nanofibers, uniaxially-aligned nanofibers deliver both architectural and immunological cues capable of promoting aligned epithelial migration. According to one embodiment, the scaffolds can be used to quantify the recruitment of MP subsets. In various embodiments, cellular and molecular mechanisms involved in microvascular remodeling and the early inflammatory host response to pro-regenerative stimulation are assessed using fluorescence microscopy and end point flow cytometry analysis of implanted materials as well as cytokine and gene expression.

Many prior animal model studies have only looked at oral mucosal healing and have not looked at ONF formation, which is a significant clinical problem; however, these prior investigations did not determine the effects on the lymphocytic infiltrate. In at least one embodiment, delivery of FTY720 nanofiber scaffolds increases the pro-regenerative monocyte population, favorably altering interleukin production and improving oral cavity wound healing.

Characterizing Drug Release Kinetics, Associated Metabolites, and Inflammatory Infiltrate in Response to Varying Doses of FTY720 Released from 50/50 PLGA/Polycaprolactone (PCL) Electro-Spun Nanofiber Meshes According to one embodiment, 1:200 drug:polymer weight ratio in PLGA-DLG-5E (high-molecular weight ester-capped PLGA) films is used to selectively recruit $Ly6C^{lo}$ monocytes from circulation into the cutaneous wound healing model. According to one embodiment, the present scaffolds are evaluated with doses of 1:20, 1:200, and 1:2000 drug:polymer weight ratio based on cutaneous wound healing experiments. In various embodiments, electrospun nanofiber meshes and/or scaffolds with the drug:polymer weight ratios are fabricated.

In one or more embodiments, biopsy punches are used to punch out identically-sized nanofiber scaffolds. In various embodiments, within the ONF models, identically sized, circular ONF (1.5 mm in diameter each) are formed. In at least one embodiment, nanofiber scaffolds of 1.5 mm in diameter are implanted in each ONF model (e.g., 10 animals, male and female, in each treatment arm). According to one embodiment, the ONF model allows for correlation of localized immune and angiogenic responses to no implant, blank scaffold, and loaded scaffold (in each of the dosages) conditions. In one or more embodiments, examination of implant-associated vasculature in each of the injury sites is performed at days 3, 5, and 7 to assess angiogenic and arteriogenic response to on-site delivery of FTY720 using PECAM staining. In various embodiments, at days 3, 5, and 7 post-injury, each of the injured hard palates is harvested for liquid chromatography mass spectrometry (LC-MS) analysis of FTY720, FTY720-p, and associated lipid metabolite concentrations to determine release kinetics and related changes in lipid metabolism in response to nanofiber scaffolds, and drug-releasing nanofiber scaffolds. In at least one embodiment, each of the injured hard palates is harvested at days 3, 5, and 7 post-injury, and digested for flow cytometric analysis of monocyte and macrophage subpopulations (CD11b, Ly6C, Ly6G, CD43, MerTK, CD64, CD206, CD301b, CCR7, CD80).

Characterizing Drug Release Kinetics, Associated Metabolites, and Inflammatory Infiltrate in Response to FTY720:Polymer (By Weight) Dose Released from (PLGA)/(PCL) Electrospun Nanofiber Meshes of Varying Degradation Rates According to one embodiment, optimal degradation of the FTY720 nanofiber scaffold determines the release of FTY720 into the adjacent mucosa, and more rapid delivery of FTY720 is associated with 80/20 PLGA/PCL (e.g., based on demonstrated correlations of lipophilic drug release and PLGA content. In at least one embodiment, the release kinetics of FTY720 in response to varying ratios of PLGA/PCL from 20/80 PLGA/PCL to 80/20 PLGA/PCL are assessed. In one or more embodiments, because of hydrophobic interactions between FTY720 and PLGA, drug release varies significantly over the ratio range.

In various embodiments, biopsy punches are used to punch out identically-sized nanofiber scaffolds. In one or more embodiments, within the ONF model, identically sized, circular hard palate injuries are made (1.5 mm in diameter each), and nanofiber scaffolds of 1.5 mm in diameter are implanted in each with 10 animals (male and female) in each treatment arm. In at least one embodiment, examination using microscopy of implant-associated vasculature in each of the injury sites is performed at days 3, 5, and 7 to assess angiogenic/arteriogenic response to on-site delivery of FTY720 using PECAM staining. According to one embodiment, at days 3, 5, and 7 post-injury, each of the hard palate mucosa is harvested for LC-MS analysis of FTY720, FTY720-p, and associated lipid metabolite concentrations to determine release kinetics and related changes in lipid metabolism in response to nanofiber scaffolds, and drug-releasing nanofiber scaffolds.

In one or more embodiments, each of the hard palate mucosal tissues is harvested at days 3, 5, and 7 post-injury, and is digested for flow cytometric analysis of monocyte and macrophage subpopulations (CD11b, Ly6C, Ly6G, CD43, MerTK, CD64, CD206, CD301b, CCR7, CD80). In various embodiments, power analysis (p=0.8, a=0.05) from flow cytometry profiling of immune subsets in oral mucosal tissue indicates a minimum sample number of 10 animals in necessary to achieve statistical significance. According to one embodiment, a minimum of 10 male and 10 female mice per group are examined using flow cytometry.

Characterizing Drug Release Kinetics, Associated Metabolites, and Inflammatory Infiltrate in Response to FTY720 Release from Mesh (Randomized Orientation) and Uniaxially-Aligned Electrospun Nanofiber Scaffolds In various embodiments, uniaxial nanofiber alignment provides improved FTY720 delivery and favorable AM monocyte recruitment compared to randomized fiber orientation based on results in cutaneous wound healing. According to one embodiment, the optimal FTY720 dosage and PLGA/PCL formulations described herein (as assessed by most favorable angiogenic/arteriogenic response and highest M2/M1 macrophage ratios) are used to fabricate both traditional electrospun scaffolds and uniaxially-aligned electrospun scaffolds with these parameters.

In one or more embodiments, to synthesize the uniaxially-aligned nanofibers, actions are performed including, but not limited to: 1) providing a collecting plate composed of a conductive substrate with a rectangular void gap in the middle; and 2) depositing vertically electrospun nanofibers (electrospun from PLGA/PCL polymer solution) in aligned fashion across the void gap (e.g., aligned deposition being facilitated by a number of electrostatic interactions). According to one embodiment, parameters of electrospinning (such as working distance, void gap width, etc.) are adjusted to created arrays (e.g., nanofiber sheets) with inter-fiber distances of about 50 µm. In at least one embodiment, biopsy punches are used to punch out identically-sized nanofiber scaffolds.

In one or more embodiments, within the ONF model, identically sized, circular hard palate mucosal injuries are created, and nanofiber scaffolds of 1.5 mm in diameter are implanted in each with 10 animals (male and female) in each treatment arm. According to one embodiment, the model allows for evaluation of localized immune and angiogenic responses to no implant, blank scaffold, and loaded scaffold in either random mesh or uniaxially-aligned nanofiber scaffolds in an internally-controlled manner. In at least one embodiment, at days 3, 5, and 7 post-injury, each of the injured hard palates is harvested for LC-MS analysis of FTY720, FTY720-P, and associated lipid metabolite concentrations to determine release kinetics and related changes in lipid metabolism in response to nanofiber scaffolds, and drug-releasing nanofiber scaffolds. In various embodiments, each of the injured hard palates is harvested at days 3, 5, and 7 post-injury, and digested for flow cytometric analysis of monocyte and macrophage subpopulations (CD11b, Ly6C, Ly6G, CD43, MerTK, CD64, CD206, CD301b, CCR7, CD80). In one or more embodiments, assessment of inflammatory mediators (Interleukin 1, 6 and 10) during ONF wound healing, with and without scaffold placement, is performed using quantitative PCR of hard palate mucosa at day 3, 5, and 7, with comparisons being made to housekeeping genes. According to one embodiment, serum evaluation of the animals assesses levels of ILL IL6, IL10 and VEGF using ELIZA to determine if there are systemic alterations in inflammatory and vasculogenic gene regulation.

Outcomes

According to one embodiment, concordance in immunomodulatory responses (high M2:M1 ratio) measured by flow cytometry and by imaging (vascularization) is observed. In at least one embodiment, tuning the dosage of FTY720 released from 1:200 drug:polymer (by weight) scaffolds alters macrophage recruitment kinetics to the injury niche to serve as biased progenitors of pro-angiogenic, anti-fibrotic host cells. In various embodiments, the present disclosure contemplates tuning the dosage to determine minimal and maximal doses at which the desired immunomodulatory response is produced. In one or more embodiments, the slower degradation rate of PLGA/PCL scaffolds (e.g., as accomplished by increasing the PCL percentage) and FTY720 release prolongs activity of pro-regenerative monocyte/macrophage populations.

In various embodiments, primary success criteria for evaluating pro-regenerative immune responses include, but are not limited to, growth and infiltration of microvascular networks. According to one embodiment, aligned nanofibers increase the cumulative release of FTY720 as compared to random (e.g., unsubstantially aligned) nanofibers (as similar results can be seen in GDNF release from aligned vs random nanofibers). In at least one embodiment, healing of the ONF using the nanofiber FTY720 scaffold demonstrates encouraging results, including that FTY720 delivery using the uniaxially-aligned scaffolds reverses ONF formation by preferentially modifying the immunomodulatory response and increasing vascularization. In one or more embodiments, the presence of FTY720 in the healing hard palate mucosal defect leads to an increase in $Ly6C^{lo}$ monocytes that were SSCloCD45+CD11b+Ly6C−Gr1− using flow cytometry and pro-regenerative cytokines using illumine and genes (i.e. IL10) using RNA-seq as the ONF heals. In various embodiments, the reparative programs of epithelial differentiation, angiogenesis, and extracellular matrix production are induced immediately following injury (e.g., compared to potential delay in the program in the ONF injury model described herein).

Additional Approaches

According to one embodiment, monocyte recruitment to sites of soft tissue injury and their ability to adhere to the endothelium are correlated with the extent of collateral arterial growth and angiogenesis. In at least one embodiment, depletion of myeloid cells in murine models of rotator cuff tear leads to vascular regression, muscle mass loss and associated reduction in fiber diameter in the adjoining supraspinatus muscle. In one or more embodiments, the present disclosure establishes a mechanistic understanding of how biomolecular cues modulate recruitment kinetics and pro-regenerative functions of monocyte subsets during oral cavity wound healing. In various embodiments, as an alternative approach to interrogate the mechanism of cell recruitment kinetics, multiple complementary loss-of-function transgenic mouse models can be employed: the CD11b-DTR transgenic mice to deplete circulating monocytes with diphtheria toxin CCR2-/-, transgenic mice with impaired IM mobilization, and NR4A1-/- mice with low AM monocyte abundance. According to one embodiment, intravenous injection of diphtheria toxin (DT) into CD11b-DTR mice causes transient but drastic reduction of circulating monocytes, without targeting granulocytes, and nearly abolishes their accumulation. In at least one embodiment, the models provide mechanistic insight into the role of non-S1P chemokine receptors that facilitate selective recruitment in muscle. In various embodiments, if there is not a clear, correlative phenotype seen with FTY720 delivery and regenerative monocyte in growth, the effects of FTY720 on the basement membrane and epithelial regeneration (e.g., as the primary target of FTY720 signaling during ONF wound healing) are evaluated.

Statistical Analysis

According to one embodiment, flow cytometric data are compared as described herein. In one or more embodiments, proliferation, apoptosis, and PECAM staining are analyzed using ANOVA testing comparing time and animal gender. In various embodiments, comparison of mRNA gene transcription is performed using $RT^2$. In some embodiments, nanofiber degradation assessment over time in vitro is measured using box analysis and using 2-sided unpaired Student t test. In at least one embodiment, μCT imaging data are compared with ANOVA and a post hoc analysis. According to one embodiment, cellular infiltrate in the implanted area are compared using ANOVA. In various embodiments, comparison of μCT imagine data and histology by blinded reviewers is performed using ANOVA comparing the gene correction models. In at least one embodiment, rigor and reproducibility is ensured by each experimental measurement being derived from 10 separate biologic specimens from male and female animals.

Currently there are thousands of patients worldwide that undergo cleft palate repair each year, and there are even more who undergo oral cavity surgery for dental and oncologic reasons. The differences between cutaneous and oral cavity wound healing are recognized, however these differences have not been explored. Various embodiments of the present disclosure focus on normal oral cavity wound phenotype and provide tools with which to tune the microenvironment of the inflammatory and pro-regenerative monocytes using FTY720 to improve healing. FTY720 is currently clinically in use to treat patients with multiple sclerosis, so the safety profiles in humans have already been determined.

In addition to wound healing, the presence of a cleft palate and/or ONF also highlights the potential for microbiologic consequences of the oral and nasal cavities being in communication, affecting the wound healing response. In one example, a dysbiosis occurs, with mixing of the oral and nasal bacteria, and the dysbiosis affects the inflammatory response to injury, altering the inflammasome, and ultimately affecting the wound healing phenotype of the patient. Thus, in the same example, determining the presence of a dysbiosis in cleft palate/ONF model and identifying the effects of dysbiosis on the inflammatory response and wound healing phenotype can augment wound healing solutions described herein.

Flow Cytometry

The following section describes one or more experimental tests, and results thereof, performed on one or more embodiments of the scaffolds described herein. The descriptions therein are provided for the purposes of illustrating various elements of the scaffolds (e.g., as observed in the one or more embodiments). All descriptions, embodiments, and the like are exemplary in nature and place no limitations on any embodiment described, or anticipated, herein or otherwise.

For analysis of lymphocyte populations, oral mucosal tissues were harvested and digested in 1 mg/ml collagenase I (Sigma) for 45 minutes at 37 degrees Celsius. For analysis of satellite cell populations, explanted oral mucosal were harvested and digested with 5,500 U/ml collagenase II and 2.5 U/ml Dispase II for 1.5 hours in a shaking 37 degrees Celsius water bath. The digested muscles were filtered through a cell strainer to obtain a single cell suspension. Single-cell suspensions from were stained for live cells using either Zombie Green or Zombie NIR (Biolegend) dyes in cell-culture grade PBS per manufacturer instructions. Cells were then stained with cell phenotyping antibodies in a 1:1 volume ratio of 3% FBS and Brilliant Stain Buffer (BD Biosciences) according to standard procedures and analyzed on a FACS AriaIIIu flow cytometer (BD Biosciences). The following antibodies were used for cell phenotyping: BV605-conjugated CD4 (Biolegend), BV785-conjugated CD8 (Biolegend), PE-Cy7-conjugated CD3ε (Biolegend), PE-conjugated anti-CD115 (BioLegend), PerCP-Cy5.5-conjugated anti-CD115 (BioLegend), PE-conjugated anti-CD25, FITC-conjugated anti-FoxP3 (eBioscience), BV510-conjugated anti-CD11b (BioLegend), BV421-conjugated anti-CD11b (BioLegend), BV510-conjugated APC (BioLegend), APC conjugated anti-Ly6C (BioLegend), BV711-conjugated anti-CD64 (BioLegend), PE-conjugated anti-MerTK (Biolegend), APC-Cy7-conjugated anti-Ly6G (BioLegend), PE-Cy7 conjugated anti-CD206 (BioLegend), FITC-conjugated anti-CD206 (BioLegend), APC-conjugated Lineage antibody cocktail (BD Pharmigen), PE-Cy5 conjugated anti-CD29 (BioLegend), PerCP-Cy5.5-conjugated anti-CXCR4 (BioLegend), 304 μL of Accucheck Counting Beads (Invitrogen) were added per sample for absolute quantification of cell populations.

Exemplary Embodiments

Referring now to the figures, for the purposes of example and explanation of the fundamental processes and components of the disclosed medical devices and methods, reference is made to FIGS. 1A-17.

Nanofiber Scaffold Fabrication

In one or more embodiments, electrospun nanofiber scaffolds are fabricated using a 1:1 weight/eight ratio of Polycaprolactone (PCL, sigma) and poly(lactic-co-glycolic-acid) (PLGA). In at least one embodiment, PLGA can be referred to as "PLAGA" (for example, in reference to PLAGA, Lakeshore Biomaterials, Birmingham, AL). In various embodiments, the polymers are dissolved in a 1:3 volume ratio solution of methanol to chloroform to achieve an 18% polymer concentration for blank fibers and 20% polymer concentration for FTY720-loaded fibers. In various embodiments, for FTY720 loaded fibers, FTY720 is added to the polymer solution at a 1:200 drug:polymer weight ratio. In one or more embodiments, each polymer solution is agitated for at least 2 hours and/or until the polymer ingredients are fully dissolved.

According to one embodiment, a polymer solution is formed (e.g., following agitation and via electrospinning or other techniques) into a plurality of uniaxially-aligned nanofibers. In at least one embodiment, uniaxial alignment generally refers to a substantially parallel arrangement of a plurality of nanofibers. In various embodiments, each of the plurality of nanofibers are substantially parallel to each other, and can be separated by a substantially constant inter-fiber distances (e.g., an average separation length between fibers). In other words, in one or more embodiments, uniaxial alignment refers to a longitudinal length of nanofibers being substantially aligned to a shared parallel.

Figure 1D:
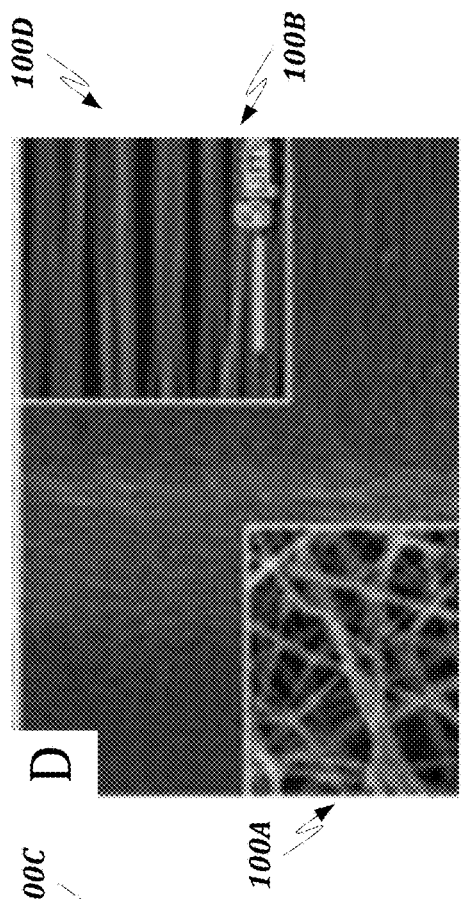
Figure 1A:
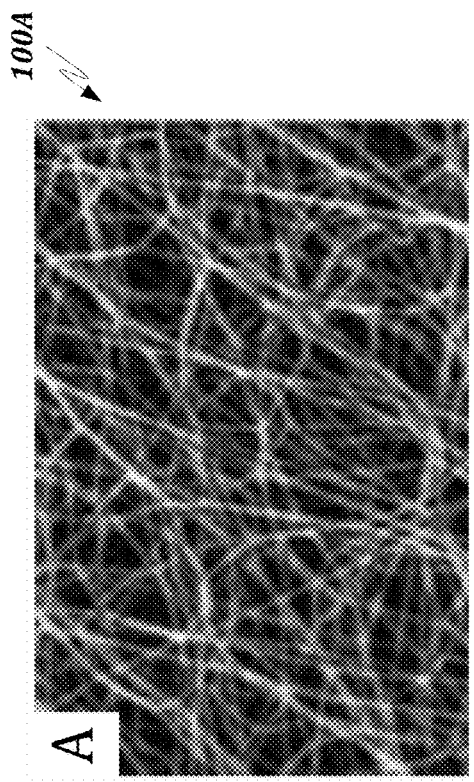
Figure 1C:
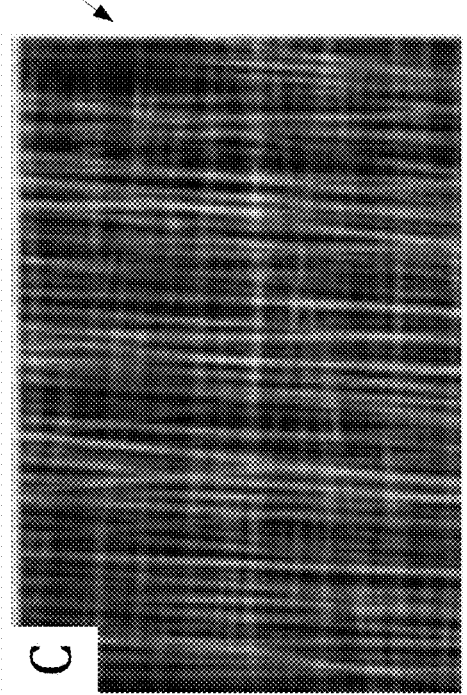

With reference to FIG. 1A (and 1D), shown are a plurality of randomly arranged nanofibers 100A. According to one embodiment, the random nanofibers 100A lack a higher order of arrangement and structure and, consequentially, do not provide directional guidance for the migration of wound healing cells (e.g., towards a wound site). With reference to FIGS. 1B-D, shown are uniaxially-aligned nanofibers 100B, 100C. In contrast to the random nanofibers 100A, in one or more embodiments, the uniaxially-aligned nanofibers 100B, 100C are arranged in a substantially parallel manner that provides direction for the migration of wound healing cells (e.g., monocytes, etc.). In other words, according to one embodiment, a uniaxial arrangement of nanofibers is advantageous for migration of cells toward a wound site, because the migration pathways (as defined by directionality of the nanofibers) are substantially identical and thus can direct cell migration in a more efficient manner (e.g., more cells migrate in the same direction toward the wound site). Conversely, in various embodiments, a random arrangement of nanofibers is less advantageous for migration of cells toward a wound site, because the migration pathways defined by the randomly arranged nanofibers directs cell migration randomly (e.g., resulting in less directed and less substantial cell migration toward a wound site). In one example, uniaxially-aligned nanofiber scaffolds promote epithelial migration along the axis of the nanofiber, and thus deliver both architectural and immunological cues capable of promoting aligned epithelial migration.

Figure 20B:
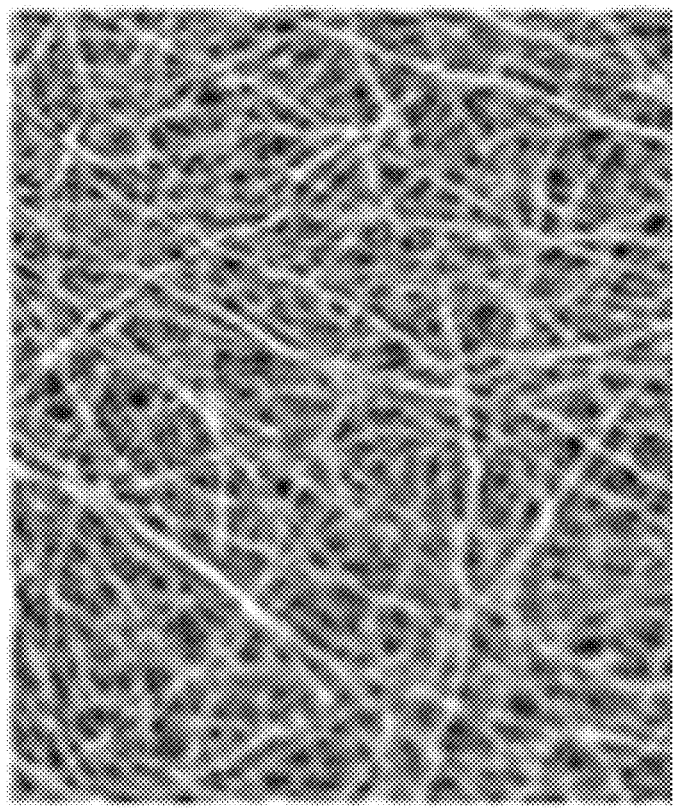
FIGS. 20A-B illustrate SEM images of exemplary blank and FTY720-doped nanofiber scaffolds, according to one embodiment of the present disclosure.
Figure 20A:
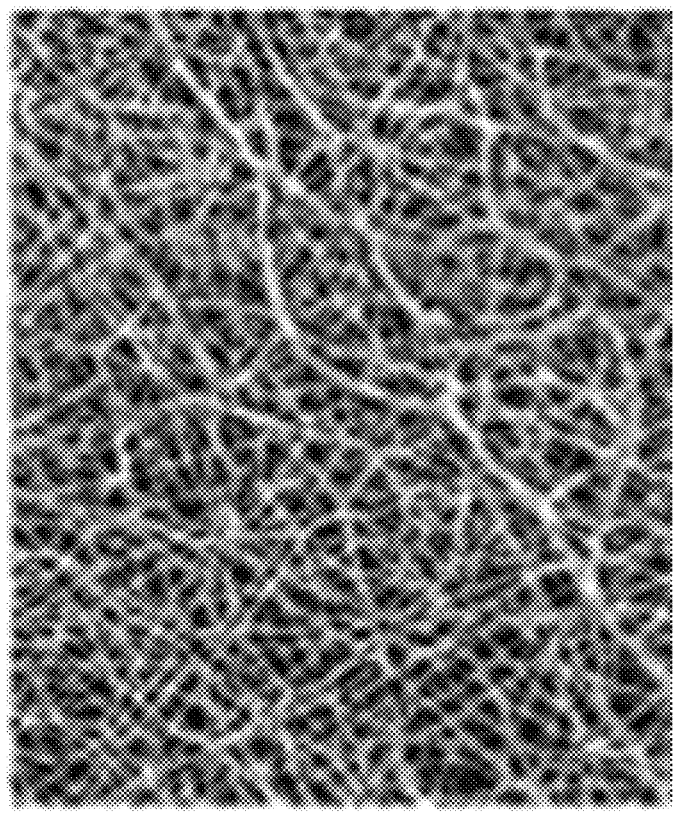

In at least one embodiment, about 2 mL of either polymer solution is loaded into a 3 mL syringe with a 10 mm diameter. According to one embodiment, to form uniaxially-aligned nanofibers (e.g., shown in FIGS. 1B-E) from each polymer solution, electrospinning is performed at a flow rate of about 1 mL/hr and at an applied voltage of about 19 kV for both blank and FTY720 nanofibers. In various embodiments, an electrospinning working distance is about 12 cm for FTY720 nanofibers and about 10 cm for blank nanofibers. With reference to FIGS. 20A-B, shown are exemplary blank nanofibers 2000A and FTY-720-doped nanofibers 2000B. According to one embodiment, the nanofibers 2000A, 2000B shown have been imaged prior to uniaxial alignment as described herein.

Figure 1F:
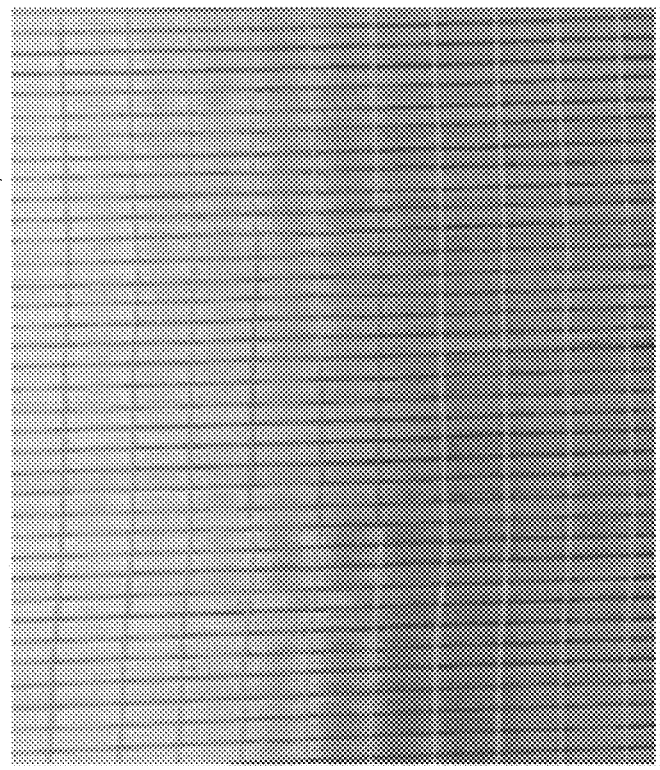
Figure 1E:
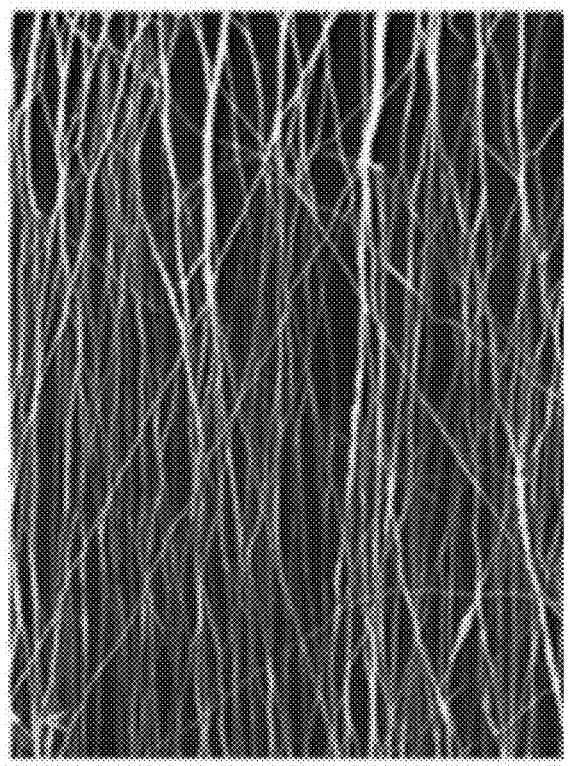
Figures 8A, 8B, 8C, 8D:
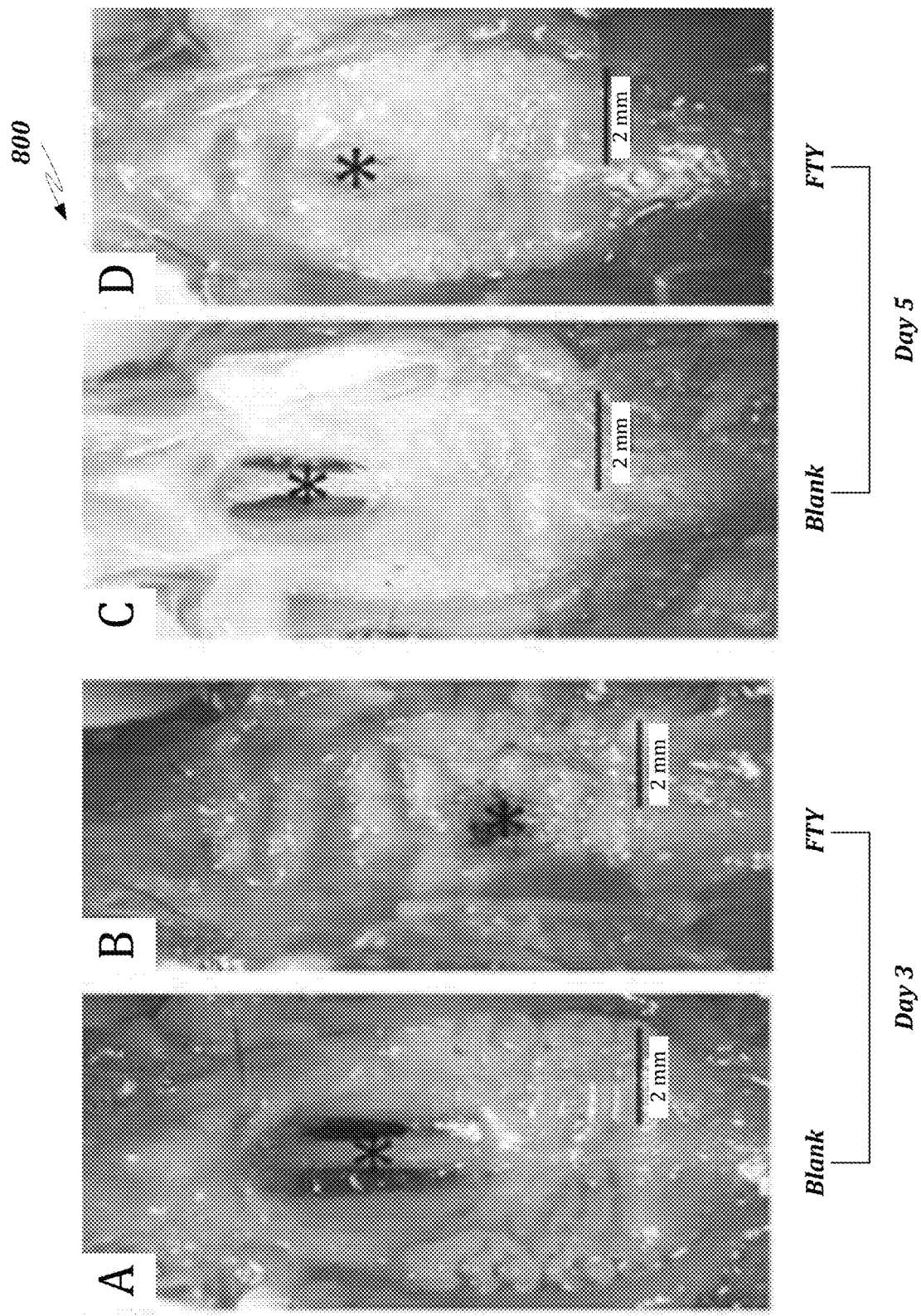
FIGS. 8A-D show exemplary ONF healing results of a blank scaffold group and an FTY720 scaffold group, according to one embodiment of the present disclosure.

In one or more embodiments, after about 2 mL of polymer is electrospun, resultant uniaxially-aligned nanofibers are wrapped in low-binding plastic folders and stored at about −20 degrees Celsius. With reference to FIG. 1F, in at least one embodiment, both blank and FTY720 uniaxially-aligned nanofibers are each arranged into nanofiber sheets 100F that may include a generally rectangular cross-section. With reference to FIG. 1H, according to one embodiment, each polymer nanofiber sheet 100F is used to fabricate a plurality of uniaxially-aligned nanofiber scaffolds 100H. In at least one embodiment, the plurality of uniaxially-aligned nanofiber scaffolds 100H are sliced and/or punched out of the nanofiber sheets 100F. According to one embodiment, FIG. 1G shows a partial, zoomed-in view of a nanofiber scaffold 100H doped with drug (e.g., such as FTY720).

For exemplary purposes only, and not limitation, FIG. 1F shows a uniaxially-aligned nanofiber sheet 100F (also referred to as a nanofiber "matrix"). It will be understood by one of ordinary skill in the art that other matrices may be utilized to the extent of using randomly oriented nanofibers (FIG. 1D), perpendicularly stacked arrays of nanofibers (e.g., a plurality of uniaxial fibers stacked atop a second plurality of uniaxial fibers, the second plurality aligned to a second parallel perpendicular to a parallel of the first plurality), or a combination of different ordered or randomized matrices.

In various embodiments, a nanofiber scaffold 100H includes a substantially flat portion 101H. According to one embodiment, the nanofiber scaffold 100H (e.g., the substantially flat portion 101H thereof) includes a substantially disk-like or cylindrical shape of a predetermined diameter. According to one embodiment, the predetermined diameter is about 1.0-20.0 mm, about 1.0-3.0 mm, about 3.0-6.0 mm, about 6.0-9.0 mm, about 9.0-12.0 mm, about 12.0-15.0 mm, about 15.0-18.0 mm, about 18.0-20.0 mm, or about 20.0-23.0 mm. In at least one embodiment, the predetermined diameter of the nanofiber scaffold 100H (or substantially flat portion 101H) is selected such that that nanofiber scaffold 100H conforms to dimensions of an ONF. In various embodiments, the nanofiber scaffold 100H includes one or more shapes including, but not limited to, circles, ovals, ellipses, quadrilaterals, and shapes of irregular geometries (such as, for example, a shape that conforms to geometry of a hard palate, or an ONF thereof). In one example, a biopsy punch is used to punch a plurality of disk-shaped, 1.5 mm diameter, uniaxially-aligned nanofiber scaffolds from one or more nanofiber sheets 100F.

Variations in electrospinning may be implemented for the fabrication of the fibrous scaffolds in utilizing artificial extracellular matrices (ECM), ECM-mimicking fibrous scaffolds, and integrating use of a variety of biocompatible polymers. In addition, the biocompatible polymers may be modified and manipulated in the process for tissue-specific applications. Biocompatible materials here may be utilized that mimic native tissues such that the nanoscale/microscale fibrous structures with interconnecting pores resemble natural ECM in tissues. As such, the porosity and interconnectivity of the pores in embodiments of the scaffold described herein facilitate cell migration and transport of nutrients for tissue repair and regeneration, depending on adjuvants or other therapeutics utilized and may facilitate attraction of M2 macrophages to the site of repair. The composition of FTY720 may therefore be modified to accommodate different applications. Thus, the scaffold and associated components are biodegradable in one aspect.

In one or more embodiments, a nanofiber scaffold includes a drug release rate (also referred to as an FTY720 release rate). In various embodiments, the drug release rate measures about 1.65-2.18 µg per 75 hours (e.g., following implantation), or about 1.91 µg per 75 hours. According to one embodiment, the nanofiber scaffold releases (from the portion of drug released in the first 75 hours) a predetermined drug portion during the first 24 hours (e.g., following implantation). In at least one embodiment, the predetermined drug portion is about 97.08-98.02%. In one or more embodiments, after about 75 hours, the nanofiber scaffold releases about 96.7% of incorporated drug. In at least one embodiment, after about 75 hours, about 0.061-0.069 µg of drug remains in the nanofiber scaffold.

As shown in FIG. 2A, a patient is imaged following two prior attempts to close an ONF after palate repair; note that each arrow defines the openings that remain between oral and nasal cavities (arrows). FIG. 2B illustrates a perspective view of a patient having a cleft palate. At FIG. 2C, an ONF remains after prior attempts to repair the cleft palate. FIG. 2D is a graphical pictorial of an exemplary installation of a nanofiber scaffold at an oral cavity wound site (e.g., such as an ONF).

Histology and Analysis

Samples used for histology sectioning had their heads dissected and palates isolated. They were placed in 10% NBF (Neutral buffered formalin), then into a histology cassette and labeled, followed by 10% formic acid decalcification reagent. Models were embedded in paraffin and cut using coronal planes in 4 µm sections, which were then stained in hematoxylin and eosin (H&E).

After staining the slides, Hamamatsu NanoZoomer 2.0 HT processor was used to scan slides and they were then analyzed in Hamamatsu NDP.view2 Viewing Software. With reference to FIG. 2, thermal injury was used to create an oral nasal fistula (ONF) in the hard palate mucosa, connecting with the nasal mucosa, similar to that seen following fistula formation in cleft palate patients. With reference to FIG. 3, following injury, the ONF heals slowly over the course of 7 days, however it is unable to completely close, creating a phenocopy of human ONF following cleft palate repair. With reference to FIG. 4, during the 7 day healing process, the mice have difficulty feeding and become weak despite being given soft chow, and ultimately more 25% die due to their inability to eat. With reference to FIGS. 5A-D, histologic analysis of the ONF reveals loss of hard palate mucosa, denuded bone and ONF formation.

To examine the monocyte and macrophage environment during ONF wound healing, flow sorting of the hard palate mucosal tissue surrounding the ONF was performed. With reference to FIGS. 6A-G, initially, pro-regenerative population of LY6Clo non-classical monocytes were compared to the LY6Chi classical monocytes. Compared to control (uninjured) hard palate mucosa, there were not significant changes in the LY6Clo or LY6Chi monocyte populations. Examination of the pro-regenerative M2 macrophage population identified an increase in the percentage of M2 macrophages at day 7 of injury compared to controls, however there was not an increase in the total number of M2 macrophages to the total macrophage population.

Figures 9A, 9B:
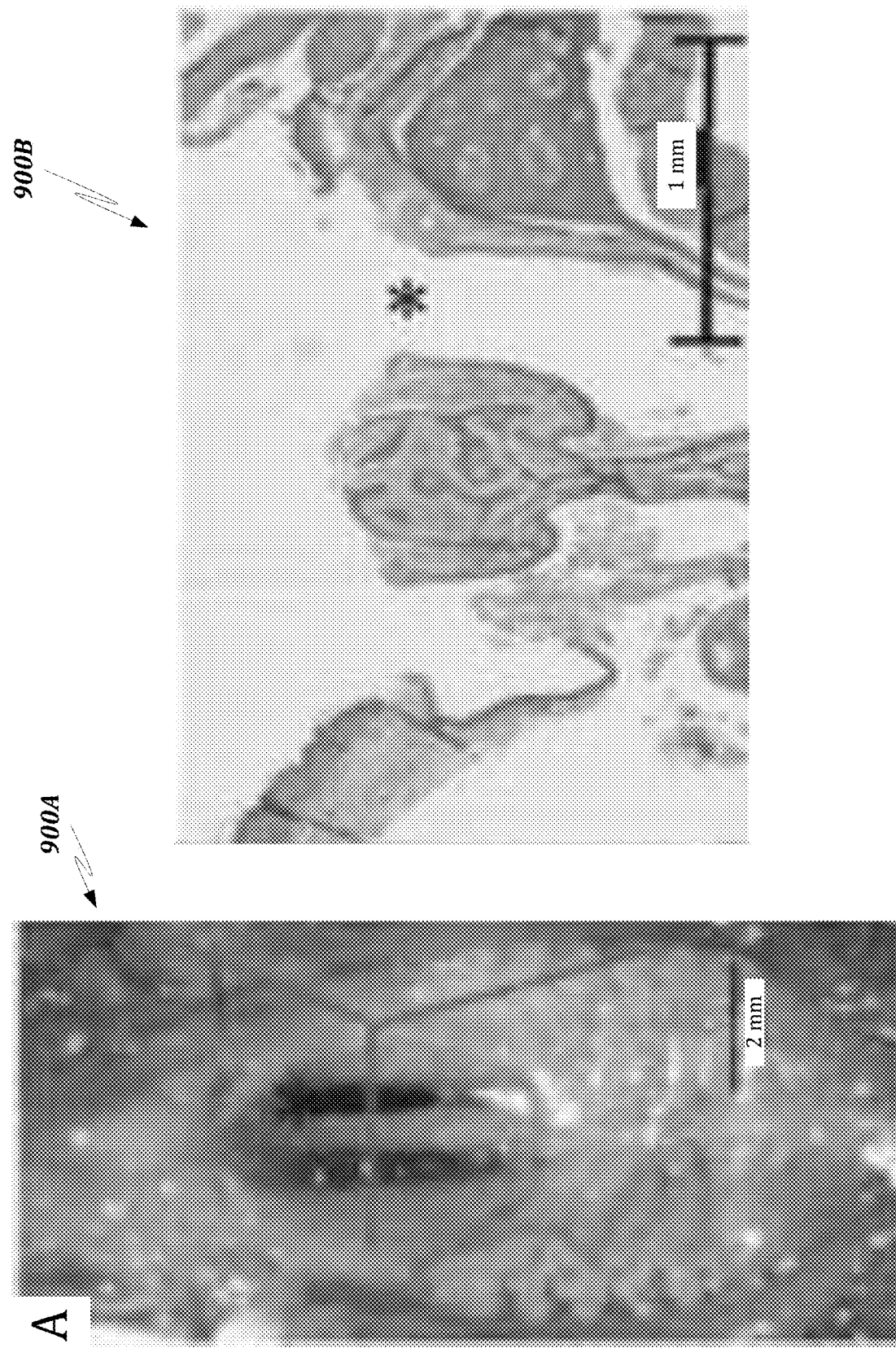
FIGS. 9A-B show a cross-section of an exemplary ONF with a blank scaffold at day 5 of a healing process, according to one embodiment of the present disclosure.

To determine if a targeted auto-therapy induction of pro-regenerative monocytes and macrophages would lead to improved ONF healing, the delivery of FTY-720, a sphingosine analog that increases pro-regenerative monocytes and macrophages was tested via a nanofiber scaffold. Following injury to the hard palate mucosa as shown in FIG. 3, blank or FTY-720 impregnated nanofiber scaffolds were implanted in the ONF sites immediately following injury as shown in FIG. 7A. With reference to FIGS. 8A-D, following scaffold placement, there was significant improvement in wound healing of the ONF with the FTY-720 scaffold at day 3 and day 5, however there was persistence of the ONF with the blank scaffold. With reference to FIGS. 9A-B, histologic examination of the injured site showed persistence of the ONF in the blank scaffold group, whereas, with reference to FIGS. 10A-B, the FTY-720 scaffold showed complete mucosalization and ongoing repair of the submucosal tissues. With reference to FIGS. 11A-D, examination of the pro-regenerative population of LY6Clo monocytes demonstrated that the insertion of the FTY-720 scaffold showed increased LY6Clo monocytes at day 3 compared to blank scaffolds, however there was no difference noted at day 5. With reference to FIGS. 12A-F, examination of the pro-regenerative M2 macrophages revealed an increase at day 3, whereas day 5 did not demonstrate any increase. With reference to FIGS. 13A-D, to examine the effects of the FTY-720 on the host inflammatory response, quantitative polymerase chain reaction (PCR) on the mucosal tissue surrounding the injury was performed and determined that IL-1 was decreased in the presence of FTY-720 whereas IL-6 and IL-10 were increased.

Additional Histology and Analysis

Oral cavity wounds are characterized by reduced inflammation, less angiogenesis, quicker healing and less scar formation. Unfortunately patients undergoing cleft palate repair suffer wound healing complications in up to 60% of patients who develop persistent oral nasal fistula (ONF). Oral cavity wound healing occurs in a bacteria-laden environment that sustains constant force as the tongue masticates food against the healing tissues. Occurrence of an ONF typically results in ongoing nasal reflux of liquid from the nose during eating and nasal air escape from the nose during speech, greatly affecting the wellbeing of the child. Currently the regenerative approach to preventing ONF formation is the use of donor-derived tissue implantation which does not harness a reparative response and exposes the patient to potential infectious transmission. Understanding the normative oral cavity wound healing response and developing targeted therapies to improve oral cavity wound healing will reduce the occurrence of ONF in children.

Oral cavity mucosal wound healing has previously been studied by creating superficial palate mucosal wounds that were found to completely re-epithelialize over a 7 day period. Healing of ONF occurred over a 7 day period following a 1.5 mm thermal injury. With reference to FIG. 2A, however, unlike the mucosal only injuries, there is persistence of the ONF causing ongoing difficulty eating. With reference to FIG. 4, the presence of an ONF was associated with 25% mortality rate in this study following injury due to dehydration and malnutrition.

A similar model of ONF was created in a mini-pig model, however these animals did not suffer from dehydration or malnutrition, although the size of the porcine ONF compared to the palate size was relatively small compared to the murine ONF reported here. Without intervention, the mini-pigs had persistence of their ONF, however several donor-derived implantable materials were used to repair the ONF with various degrees of success. Histologic evaluation of the mini-pigs demonstrated complete re-epithelialization of the palate and closure of the ONF. Using palate mucosal injury models, investigators have evaluated multiple therapeutic targets to aid in wound healing including VEGFa and Thymosin B4. These studies have highlighted the inflammatory, histologic, and transcriptional differences between cutaneous and oral cavity wound healing and suggest that these differences can be targeted using regenerative approaches to improve oral cavity wound healing.

Monocytes are a key component of wound healing and are present during cutaneous and oral cavity wound healing. According to one embodiment, oral cavity wounds have fewer monocytes present compared to cutaneous wounds. Monocytes in mice can take on a pro-inflammatory (Ly6C hi) and a pro-reparative (Ly6Clo) phenotype. Once in the tissue, the monocytes can differentiate into macrophages that also play an important role in wound repair and they assume two phenotypes M1 (inflammatory) or M2 (pro-reparative).

With reference to FIGS. 6A-G, the presence of Ly6Chi and Ly6Clo monocytes did not change following injury or over the course of ONF healing. However, evaluation of the total macrophage population revealed an increase of total macrophages and M2 macrophages as a % of total macrophages at day 7, when the ONF wound had matured and there was little evidence of scar formation. Evaluation of cutaneous wounds demonstrated that inhibition of M2 macrophage production was associated with prolonged wound healing and more inflammation, suggesting that M2 macrophages are critical to reduced scarring and inflammation.

Multiple approaches have been used to improve the recruitment of the pro-regenerative monocytes and macrophages to cutaneous wounds. According to one embodiment, FTY720, a sphingosine analog, demonstrates efficacy in attracting pro-regenerative monocytes to cutaneous and oronasal wounds. As outlined in FIG. 19, the delivery of FTY720 on a nanofiber scaffold increased the frequency of Ly6Clo pro-regenerative monocytes at 3 days and was associated with improved wound healing. In at least one embodiment, FTY720 increases the migration of M2 macrophages into a wound bed (e.g., in the hard palate). With reference to FIGS. 7, 9, and 14, the data demonstrate that FTY720 delivery on a nanofiber scaffold following hard palate mucosal injury leads to wound contracture at day 5 and complete healing at day 7 compared to the blank scaffold where there was persistence of the ONF. With reference to FIGS. 15A-D, evaluation of the monocyte and macrophage population during the healing process following hard palate mucosal injury revealed an increase in Ly6Clo monocytes in the wound bed compared to blank scaffolds, similar to the results found in the cutaneous wound healing studies.

With reference to FIGS. 6A-G, 11A-D and 14A-I, the FTY720 nanofiber delivery increased the proportion of M2 macrophages in the wound bed at day 3 (FIGS. 11A-D), instead of day 7 as seen in the control mice (FIGS. 6A-G, 14A-I), as reported above. The secretion of interleukins during oral wound healing is critical, as inhibition of their function is associated with reduced macrophage infiltration, angiogenesis and collagen deposition. During wound healing monocytes and macrophages produce multiple cytokines, particularly ILL during the immediate inflammatory response. Prior reports have demonstrated that high levels of IL1 are associated with poor wound healing, however complete loss of IL1 leads to delayed wound healing particularly in the oral cavity. The present results demonstrated that delivery of the FTY720 nanofiber reduced the expression of IL1 and IL6 seen in the blank scaffolds. Pro-regenerative interleukins include IL10. With reference to FIGS. 13A-C, the present results demonstrate that treatment with the FTY720 nanofiber was associated with decreased expression of IL6 and increased expression of IL10 expression compared to blank nanofibers.

Oral cavity wound healing occurs in a bacteria laden environment and there is constant physical trauma to the healing tissues. Clinically, ONF formation occurs commonly after cleft palate repair and currently available therapies to reduce ONF formation do not harness the innate immune system. Delivery of FTY720 nanofiber scaffolds improves oral cavity wound healing and prevents ONF formation by increasing pro-regenerative monocyte and macrophage infiltration, and by inducing favorable interleukin expression.

Preliminary Studies

The following section describes one or more experimental tests, and results thereof, performed on one or more embodiments of the scaffolds described herein. The descriptions therein are provided for the purposes of illustrating various elements of the scaffolds (e.g., as observed in the one or more embodiments). All descriptions, embodiments, and the like are exemplary in nature and place no limitations on any embodiment described, or anticipated, herein or otherwise.

Development of a murine ONF model was accomplished using 12 week old mice with a midline 1.5 mm ONF injury in the hard palate. With reference to FIG. 4, the functional outcomes of dehydration and survival were compared at 7 days, where 27% of mice died at day 7 due to dehydration from poor oral intake. With reference to FIGS. 7A-C, over the course of 7 days, there was gradual healing and narrowing of the ONF. The initial injury is associated with exposure of the midline vomer bone, similar to that in humans, and it narrows over the following 7 days. At the 7th day, there is narrowing of the ONF, however there is persistence of the ONF, making it difficult for the mice to eat and requiring soft chow.

With reference to FIGS. 9A-B, histological staining of the hard palate through the ONF at day 5 revealed apparent attempts of re-epithelialization at the edges of the wound, but a direct connection between the oral cavity and the nasal cavity persisted. With reference to FIGS. 14A-I, flow cytometric analysis of the hard palate mucosal at day 3 and 5 monocyte population did not reveal significant differences in the Ly6Clo (regenerative) and Ly6Chi (inflammatory) cell populations. The presence of Ly6Chi and Ly6Clo monocytes did not change following injury or over the course of ONF healing. However, evaluation of the total macrophage population revealed an increase of total macrophages and M2 macrophages as a % of total macrophages at day 7, when the ONF wound had matured and there was little evidence of scar formation.

Preliminary Studies

The following section describes one or more experimental tests, and results thereof, performed on one or more embodiments of the scaffolds described herein. The descriptions therein are provided for the purposes of illustrating various elements of the scaffolds (e.g., as observed in the one or more embodiments). All descriptions, embodiments, and the like are exemplary in nature and place no limitations on any embodiment described, or anticipated, herein or otherwise.

Figures 10A, 10B:
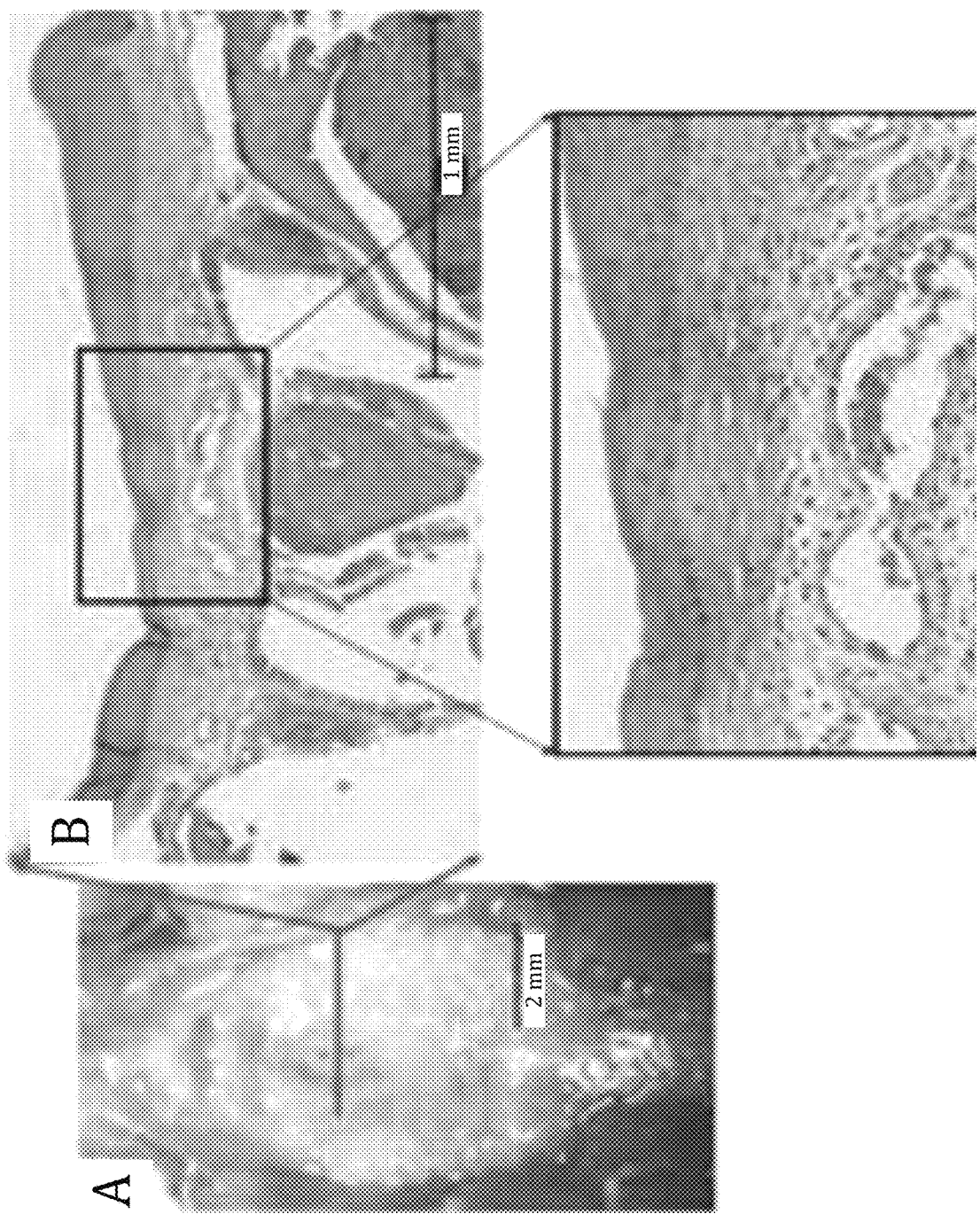
FIGS. 10A-B show a cross-section of an exemplary ONF with an FTY720 scaffold at day 5 of a healing process, according to one embodiment of the present disclosure.

With reference to FIGS. 8A-D, placement of the FTY720 nanofiber scaffold, compared to a blank scaffold, had a profound effect on oral cavity healing with drastic reduction of ONF at day 3 and closure of the ONF at day 5. With reference to FIGS. 10A-B, at day 5 there was reconstitution of the oral cavity epithelium and there was not communication between the oral and nasal cavities. With reference to FIGS. 11A-D, evaluation of the monocyte and macrophage population during the healing process following hard palate mucosal injury revealed an increase in Ly6Clo (AM) monocytes in the wound bed compared to blank scaffolds, similar to the results found when FTY720 was applied to cutaneous wound healing studies. Further, with reference to FIGS. 12A-F, FTY720 nanofiber delivery increased the proportion of M2 macrophages in the wound bed at day 3, instead of day 7 as seen in the control untreated mice, and these data are also consistent with the findings seen in the delivery of FTY720 nanofibers during cutaneous wound healing.

With reference to FIGS. 13A-C, treatment with the FTY720 nanofiber was also associated with increased expression of IL10 expression compared to blank nanofibers at day 3 following injury. With reference to FIG. 17, $\mu$CT evaluation of the palatine and surrounding hard palate bones did not reveal any changes to the underlying bone in the control or the FTY720 treated mice following ONF creation.

Investigating the Ability of Uniaxially-Aligned
Nanofibers Releasing FTY720 to Improve Oral
Cavity Wound Healing in an ONF Model In at least one embodiment, implanting, to a hard palate wound site, an optimally designed nanofiber FTY720 mesh scaffold improves palate wound healing and reduces ONF formation through the selective recruitment of pro-regenerative monocytes. In various embodiments, the optimally designed nanofiber meshes described herein (e.g., and as determined by optimal dose, release kinetics, and alignment of the nanofiber scaffold) are used to create FTY720 and control (blank) nanofiber scaffolds using an ONF model with 10 animals in each treatment arm. According to one embodiment, wound healing of the ONF after scaffold placement is assessed at day 3, 5 and 7 using histomorphometry, H+E, PECAM staining (to evaluate endothelial regeneration) and $\mu$CT scanning with angiography (to evaluate changes to underlying bone). At days 3, 5, and 7 following ONF injury and scaffold placement, the hard palate tissues are harvested and digested for flow cytometric analysis of monocyte and macrophage subpopulations (CD11b, Ly6C, Ly6G, CD43, MerTK, CD64, CD206, CD301b, CCR7, CD80). In various embodiments, the ONF wounds are evaluated for vascularization using PECAM staining, matrix deposition using stains for laminin and type IV collagen, as well as Masson's Trichrome staining, all of which are quantified using ImageJ. In at least one embodiment, proliferation and apoptosis assays are performed as described herein.

In various embodiments, to quantify neovascular branching, contrasted $\mu$CT imaging is performed. According to one embodiment, specimens are prepared according to methods described herein. In one or more embodiments, the vasculature is injected with barium compound (90 bloom) over constant pressure using an infusion pump after vessel fixation. In at least one embodiment, mouse palates are dissected and fixed in formalin. With reference to FIG. 18, in various embodiments, maxilla are scanned using a high-resolution $\mu$CT (16-$\mu$M isotropic voxel size). According to one embodiment, the kidney and liver are scanned to ensure even perfusion as a control. In one or more embodiments, the maxilla are decalcified in formic acid and rescanned with $\mu$CT imaging. In various embodiments, vessel volume, connectivity, number, thickness, separation, and degree of anisotropy are evaluated using Scanco40 $\mu$CT imaging systems. With reference to FIG. 18, in at least one embodiment, proof of concept of contrasted $\mu$CT angiography demonstrates the greater palatine artery (red) and the smaller capillaries (green) adjacent to them are used to compare vascularization following injury.

Determining the Changes in Inflammatory
Cytokines and Gene Expression After the Delivery
of Uniaxially-Aligned Nanofibers Releasing
FTY720 During Palate Wound Healing According to one embodiment, delivery of FTY720 uniaxially-aligned nanofibers during oral cavity wound healing changes the cytokine and gene expression to a pro-regenerative signature. In one or more embodiments, the ability of FTY720 to improve oral cavity wound healing using an ONF model is supported by data shown in FIGS. 14A-I and described herein. With reference to FIG. 19, according to one embodiment, a uniaxially-aligned, FTY720-releasing nanofiber scaffold influences a healing process 1900 such that expression of pro-regenerative interleukins (e.g., IL10) is increased and the expression of pro-inflammatory interleukins (e.g., ILL IL4, IL6) is reduced. In at least one embodiment, the nanofiber scaffold causes, during the healing process 1900, increased expression of keratinocytes (e.g., that stimulate melanocyte functions such as proliferation, differentiation, melanogenesis, and dendritogenesis) and transcription factors thereof, such as Sox2.

In at least one embodiment, to determine the pro-regenerative signature, collection of hard palate mucosa of mice for cytokine and RNA-seq prior to oral injury (e.g., and at day 3, 5, and 7 following injury from 5 male and 5 female mice) is performed. In various embodiments, the cytokine analysis (for example, a Chemokine 36 array, Thermo Fisher) undergoes analysis in the Emory Multiplex Assay Core. According to one embodiment, RNA-seq data is generated using the Emory Genomics Core. In one or more embodiments, about 50 million paired-end 100 nt reads per sample are mapped to the human reference genome using the R/Bioconductor package DEXSeq (e.g., which is optimized for robust inference of annotated exon usage, and uses a generalized linear model for hypothesis testing accounting for biological and technical variability). In at least one embodiment, quantitative PCR is performed on the cells to confirm changes noted by RNA-seq. In various embodiments, the cells are analyzed for changes in ILL IL6 and IL10 and downstream targets. According to one embodiment, Pathway analysis of RNA-seq data using Ingenuity software package (Qiagen) focuses on proliferation, differentiation, migration, angiogenesis and extracellular matrix production.

CONCLUSION

The embodiments were chosen and described in order to explain the principles of the claimed inventions and their practical application so as to enable others skilled in the art to utilize the inventions and various embodiments and with various modifications as are suited to the particular use contemplated. Alternative embodiments will become apparent to those skilled in the art to which the claimed inventions pertain without departing from their spirit and scope. Accordingly, the scope of the claimed inventions is defined by the appended claims rather than the foregoing description and the exemplary embodiments described therein.

What is claimed is:

1. An implantable scaffold comprising:
a plurality of nanofibers forming a flat portion having a diameter between 1 mm and 23 mm;
wherein all of the nanofibers within the plurality of nanofibers are uniaxially aligned; and
wherein each of the plurality of nanofibers comprises polycaprolactone (PCL), poly (lactic-co-glycolic-acid) (PLGA), and an S1P1 agonist;
wherein the S1P1 agonist is differentially released for controlled release with an initial burst release in the first hours, followed by a delay, and a second phase of release occurring between 3 and 5 days following implantation;
wherein the plurality of nanofibers is configured to release between 93.87% and 94.78% of the S1P1 agonist within the first 24 hours following implantation;
wherein the plurality of nanofibers is configured to release about 96.7% of the S1P1 agonist after about 75 hours following implantation; and
wherein the S1P1 agonist is FTY720.

2. The implantable scaffold of claim 1, wherein each of the plurality of nanofibers comprises PCL and PLGA at a predetermined weight ratio between about 20:80 and 80:20 wt./wt.

3. The implantable scaffold of claim 2, wherein:
the predetermined weight ratio of PCL and PLGA is about 1:1 wt./wt.; and
each of the plurality of nanofibers comprises FTY720 at about a 1:200 drug: polymer weight ratio.

4. The implantable scaffold of claim 3, wherein the flat portion comprises a disk-like shape.

5. The implantable scaffold of claim 3, wherein the plurality of nanofibers comprises inter-fiber distances of about 50 μm.

6. The implantable scaffold of claim 1, wherein the implantable scaffold is configured to selectively recruit LY6C$^{lo}$ monocytes and M2 macrophages to oral cavity wounds when implanted therein.

7. An implantable scaffold, comprising:
a plurality of uniaxially aligned nanofibers, wherein all the nanofibers within the plurality of nanofibers are uniaxially aligned,
wherein the plurality of nanofibers comprises polycaprolactone (PCL), poly (lactic-co-glycolic-acid) (PLGA), and between 1.7 and 2.2 μg of an S1P1 agonist,
wherein the S1P1 agonist is differentially released for controlled release with an initial burst release in the first hours, followed by a delay, and a second phase of release occurring between 3 and 5 days following implantation,
wherein the plurality of nanofibers is configured to release between 93.87% and 94.78% of the S1P1 agonist within the first 24 hours following implantation; and
wherein the S1P1 agonist is FTY720.

8. The implantable scaffold of claim 7, wherein the plurality of nanofibers is configured to release about 96.7% of the S1P1 agonist after about 75 hours following implantation.

9. The implantable scaffold of claim 7 wherein each of the plurality of nanofibers comprises PCL and PLGA at a predetermined weight ratio between about 20:80 and 80:20 wt./wt.

10. The implantable scaffold of claim 7, wherein:
the predetermined weight ratio of PCL and PLGA is about 1:1 wt./wt., the S1P1 agonist is FTY720, and each of the plurality of nanofibers comprises FTY720 at about a 1:200 drug: polymer weight ratio.

11. An implantable scaffold, comprising:
a plurality of uniaxially aligned nanofibers forming a flat portion having a diameter of between 1 mm and 23 mm, all of the nanofibers within the plurality of nanofibers being uniaxially aligned;
wherein each of the plurality of nanofibers comprises polycaprolactone (PCL), poly (lactic-co-glycolic-acid) (PLGA), and an S1P1 agonist,
wherein the S1P1 agonist is differentially released with an initial burst release in the first hours, followed by a delay, and a second phase of release occurring between 3 and 5 days;
wherein the S1P1 agonist is FTY720;
wherein the plurality of nanofibers is configured to release between 93.87% and 94.78% of the S1P1 agonist within the first 24 hours following implantation, and
wherein the implantable scaffold selectively recruits LY6C$^{lo}$ monocytes and M2 macrophages to an implantation site.

12. The implantable scaffold of claim 11, wherein 3 days after implantation of the implantable scaffold in a wound site, the LY6C$^{lo}$ monocytes are recruited in an amount between 11% and 125% greater than an amount recruited upon implantation of an identical implantable scaffold without the S1P1 agonist.

13. The implantable scaffold of claim 11, wherein 3 days after implantation of the implantable scaffold in a wound site, the M2 macrophages are recruited in an amount between 45.3% and 138.5% greater than an amount recruited upon implantation of an identical implantable scaffold without the S1P1 agonist.

14. The implantable scaffold of claim 11, wherein the plurality of nanofibers is configured to release about 96.7% of the S1P1 agonist after about 75 hours following implantation.

* * * * *